(12) United States Patent
Boiteau et al.

(10) Patent No.: US 7,879,907 B2
(45) Date of Patent: Feb. 1, 2011

(54) 3-PHENYLPROPANOIC COMPOUND ACTIVATORS OF RECEPTORS OF PPAR TYPE AND PHARMACEUTICAL/COSMETIC COMPOSITIONS COMPRISED THEREOF

(75) Inventors: Jean-Guy Boiteau, Valbonne (FR); Laurence Clary, La Colle sur Loup (FR); Jean-Claude Pascal, Nice (FR); Veronique Parnet, Le Cannet (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 12/632,159

(22) Filed: Dec. 7, 2009

(65) Prior Publication Data
US 2010/0158843 A1 Jun. 24, 2010

Related U.S. Application Data

(63) Continuation of application No. PCT/FR2008/050996, filed on Jun. 4, 2008.

(30) Foreign Application Priority Data
Jun. 5, 2007 (FR) .................................. 07 55476

(51) Int. Cl.
A61K 31/235 (2006.01)
A61K 31/185 (2006.01)
C07C 317/14 (2006.01)
C07C 69/76 (2006.01)
C07C 229/00 (2006.01)
C07C 59/00 (2006.01)
C07C 65/01 (2006.01)

(52) U.S. Cl. .................. 514/543; 514/576; 560/11; 560/75; 562/429; 562/452; 562/465

(58) Field of Classification Search .................. None
See application file for complete search history.

(56) References Cited

U.S. PATENT DOCUMENTS 6,927,228 B2  8/2005  Bernardon et al.
7,470,807 B2 * 12/2008  Shoda et al. .................. 560/56

FOREIGN PATENT DOCUMENTS

| WO | WO 99/62871 A1 | 12/1999 |
| WO | WO 01/40172 A1 | 6/2001 |
| WO | WO 02/12210 A1 | 2/2002 |
| WO | WO 2007/049158 A2 | 5/2007 |

\* cited by examiner

*Primary Examiner*—Paul A Zucker
(74) *Attorney, Agent, or Firm*—Buchanan Ingersoll & Rooney, P.C.

(57) ABSTRACT

Novel 3-phenylpropanoic acid compounds have the general formula (I) below:

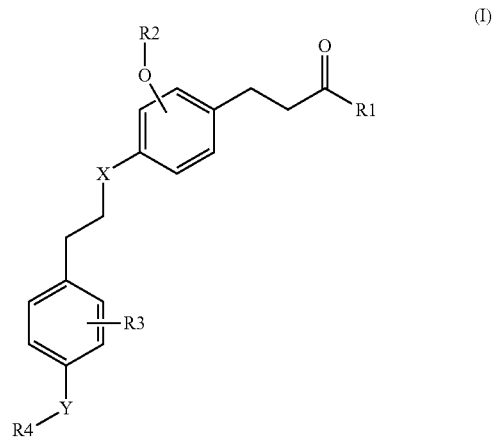

and are formulated into pharmaceutical compositions for administration in human or veterinary medicine (in dermatology, and also in the field of cardiovascular diseases, immune diseases and/or lipid metabolism-related diseases), or, alternatively, into cosmetic compositions.

22 Claims, 4 Drawing Sheets

3-PHENYLPROPANOIC COMPOUND ACTIVATORS OF RECEPTORS OF PPAR TYPE AND PHARMACEUTICAL/COSMETIC COMPOSITIONS COMPRISED THEREOF

CROSS-REFERENCE TO PRIORITY/PCT APPLICATIONS

This application claims priority under 35 U.S.C. §119 of FR 0755476, filed Jun. 5, 2007, and is a continuation of PCT/FR 08/050,996, filed Jun. 4, 2008, and designating the United States (published in the French language on Dec. 18, 2008 as WO 2008/152333 A2; the title and abstract were also published in English), each hereby expressly incorporated by reference and each assigned to the assignee hereof.

BACKGROUND OF THE INVENTION

1. Technical Field of the Invention

The present invention relates to, as novel and useful industrial products, a novel class of 3-phenylpropanoic acid compounds that activate the Peroxisome Proliferator-Activated Receptor type receptors of subtype γ (PPARγ). This invention also relates to the process for preparing such compounds and formulation into pharmaceutical compositions for administration in human or veterinary medicine, or alternatively in cosmetic compositions.

2. Description of Background and/or Related and/or Prior Art

The activity of receptors of PPAR type has been the subject of numerous studies. See, as a guide, the publication entitled "Differential Expression of Peroxisome Proliferator-Activated Receptor Subtypes During the Differentiation of Human Keratinocytes", Michel Rivier et al., J. Invest. Dermatol. 111, 1998, pp. 1116-1121, in which is listed a large number of bibliographic references relating to PPAR type receptors. Also see, as a guide, the file entitled "The PPARs: From orphan receptors to Drug Discovery", Timothy M. Willson, Peter J. Brown, Daniel D. Sternbach, and Brad R. Henke, J. Med. Chem., 2000, Vol. 43, pp. 527-550.

The PPAR receptors activate transcription by binding to DNA sequence elements known as the peroxisome proliferator response elements (PPRE), in the form of a heterodimer with the retinoid X receptors (known as RXRs).

Three subtypes of human PPAR have been identified and described: PPARα, PPARγ and PPARδ (or NUC1).

PPARα is mainly expressed in the liver, whereas PPARδ is ubiquitous.

Of the three subtypes, PPARγ is the one that has been the most extensively studied. All the references suggest a critical role of PPARγ in the regulation of differentiation of adipocytes, where it is strongly expressed. It also plays a key role in systemic lipid homeostasis.

It has especially been described in WO 96/33724 that PPARγ-selective compounds, such as a prostaglandin-J2 or -D2, are potential active agents for the treatment of obesity and diabetes.

Moreover, the Assignee hereof has already described in WO 02/12210, WO 03/055 867 and WO 2007/049 158 the formulation of biaromatic compounds that activate PPARγ type receptors into pharmaceutical compositions, such compositions being useful for treating skin disorders associated with an anomaly of epidermal cell differentiation.

It nevertheless remains necessary to develop novel such compounds that have good activity and advantageous pharmaceutical properties.

SUMMARY OF INVENTION

Novel 3-phenylpropanoic acid compounds have now been developed that have, surprisingly, activity towards the PPARγ receptors.

The molecules described in WO 2007/049 158 absorb UV at wavelengths above 290 nm as a result of their conjugated structures. In contrast, for the compounds of the present invention, there is no absorption in this wavelength range (290-700 nm). This absence of absorption advantageously reduces the risks of phototoxicity and of photo-genotoxicity of the compounds of the present invention, which increases the safety for the user in the case of pharmaceutical or cosmetic compositions applied topically.

Moreover, the compounds according to the present invention are usually obtained in solid form, which has the advantage of enabling their easy purification at the industrial scale by employing techniques such as recrystallization. The use of solid compounds for the preparation of pharmaceutical and/or cosmetic compositions also has a real advantage in the context of their pharmaceutical and/or cosmetic development on account of the virtually nonexistent content of residual solvents that these compounds contain, when compared with that which they may contain when they are in the form of an oil.

Thus, the present invention features compounds corresponding to the general formula (I) below:

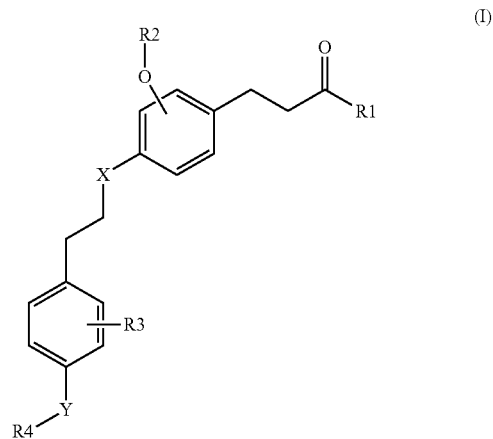

in which:

$R_1$ is a hydroxyl radical or an alkoxy radical;

$R_2$ is a hydrogen atom, an alkyl radical, a cycloalkyl radical, an optionally substituted aralkyl radical or a polyether radical;

$R_3$ is a hydrogen atom, a halogen, an alkyl radical or an alkoxy radical;

$R_4$ is an alkyl radical, an optionally substituted aryl radical or an optionally substituted aralkyl radical;

X is an oxygen atom or a radical $CH_2$;

Y is an oxygen atom, a radical $NR_5$ or a radical $OSO_2$, OCO, $NR_5CO$ or $NR_5SO_2$;

$R_5$ is a hydrogen atom or an alkyl radical;

and also the salts thereof with a pharmaceutically acceptable acid or base, the pharmaceutically acceptable solvates and hydrates thereof.

DETAILED DESCRIPTION OF BEST MODE AND SPECIFIC/PREFERRED EMBODIMENTS OF THE INVENTION

In particular, when the compounds according to the invention are in the form of a salt, it is a salt of an alkali metal, in particular a sodium or potassium salt, or a salt of an alkaline-earth metal, in particular of magnesium or calcium, or alternatively a salt with an organic amine, more particularly with an amino acid such as arginine or lysine.

When the compounds according to the invention bear an amine function and are in the form of a salt of this amine, it is a salt of a mineral acid, for instance hydrochloric acid, sulfuric acid or hydrobromic acid, or a salt of an organic acid, for instance acetic acid, triflic acid, tartaric acid, oxalic acid, citric acid, trifluoroacetic acid or methanesulfonic acid.

According to the present invention, the term "alkyl radical" means a linear or branched saturated hydrocarbon-based chain containing from 1 to 12 carbon atoms and more particularly from 1 to 6 carbon atoms.

Preferably, the alkyl radicals according to the present invention are selected from methyl, ethyl, propyl, isopropyl, butyl, isobutyl, tert-butyl, pentyl, isoamyl, amyl, hexyl, heptyl, octyl and decyl radicals. More particularly, the alkyl radicals are selected from methyl, ethyl, propyl, isopropyl, butyl, isobutyl, tert-butyl, pentyl, isoamyl, amyl and hexyl radicals.

According to the present invention, the term "lower alkyl radical" means an alkyl radical as defined previously and containing from 1 to 4 carbon atoms and advantageously 1 to 3 carbon atoms. Thus, preferably, such radicals are selected from methyl, ethyl, propyl, isopropyl, butyl, isobutyl and tert-butyl radicals.

According to the present invention, the term "cycloalkyl radical" means a saturated cyclic hydrocarbon-based chain containing from 3 to 7 carbon atoms.

Preferably, the cycloalkyl radical is selected from cyclopropyl, cyclobutyl, cyclopentyl, cyclohexyl and cycloheptyl radicals.

According to the present invention, the term "aryl radical" means an unsubstituted phenyl or naphthyl.

According to the present invention, the term "substituted aryl radical" means a phenyl or a naphthyl substituted with one or more atoms or groups of atoms selected from: alkyl, alkoxy, halogen, hydroxyl, cyano, trifluoromethyl and nitro.

Preferably, the substituted aryl radical is selected from phenyl radicals monosubstituted with a halogen.

According to the present invention, the term "aralkyl radical" means an alkyl substituted with an unsubstituted phenyl or naphthyl.

Preferably, the aralkyl radical is a benzyl or phenethyl radical.

According to the present invention, the term "substituted aralkyl radical" means an aralkyl radical substituted with one or more atoms or groups of atoms selected from: alkyl, alkoxy, halogen, hydroxyl, cyano, trifluoromethyl and nitro.

The substituted aralkyl radical is preferably selected from phenethyl radicals monosubstituted with a lower alkyl radical and benzyl radicals monosubstituted with a halogen.

According to the present invention, the term "halogen atom" means a fluorine, chlorine, bromine or iodine atom.

According to the present invention, the term "hydroxyl radical" means the radical —OH.

According to the present invention, the term "alkoxy radical" means an oxygen atom substituted with an alkyl moiety.

The alkoxy radicals are preferably methoxy, ethoxy, isopropyloxy, n-propyloxy, tert-butoxy, n-butoxy, n-pentyloxy and n-hexyloxy radicals.

According to the present invention, the term "lower alkoxy radical" means an oxygen atom substituted with a lower alkyl radical.

According to the present invention, the term "polyether radical" means a radical containing from 1 to 7 carbon atoms interrupted with at least one oxygen atom. Preferably, the polyether radical is selected from radicals such as methoxyethoxy, ethoxyethoxy, methoxyethyl, ethoxyethyl and methoxyethoxyethoxy.

Among the compounds of general formula (I) above according to the present invention, especially preferred are the following compounds (alone or as a mixture):

1. 3-{-4-[3-(4-benzyloxy-3-methoxyphenyl)propyl]-3-butoxyphenyl}propanoic acid;
2. 3-{3-butoxy-4-[3-(4-ethoxy-3-methoxyphenyl)propyl]phenyl}propanoic acid;
3. 3-{3-butoxy-4-[3-(4-butoxy-3-methoxyphenyl)propyl]phenyl}propanoic acid,
4. 3-{3-butoxy-4-[3-(4-methanesulfonyloxy-3-methoxyphenyl)propyl]phenyl}propanoic acid;
5. 3-(4-{3-[4-(butane-1-sulfonyloxy)-3-methoxyphenyl]propyl}-3-butoxyphenyl)propanoic acid;
6. 3-{3-butoxy-4-[3-(4-ethanesulfonyloxy-3-methoxyphenyl)propyl]phenyl)propanoic acid;
7. 3-[4-{3-[4-(butane-1-sulfonyloxy)-3-methoxyphenyl]propyl}-3-(3-fluorobenzyloxy)phenyl]propanoic acid;
8. 3-[4-{3-[4-(butane-1-sulfonyloxy)-3-methoxyphenyl]propyl}-3-(4-fluorobenzyloxy)phenyl]propanoic acid;
9. 3-(4-{3-[4-(butane-1-sulfonyloxy)-3-methoxyphenyl]propyl}-3-cyclopropylmethoxyphenyl)propanoic acid;
10. 3-[4-{3-[4-(butane-1-sulfonyloxy)-3-methoxyphenyl]propyl}-2-(3-methoxybenzyloxy)phenyl]propanoic acid;
11. 3-(4-{3-[4-(butane-1-sulfonyloxy)-3-methoxyphenyl]propyl}-2-butoxyphenyl)propanoic acid;
12. methyl 3-[4-[3-(4-acetylaminophenyl)propyl]-3-(2-methoxyethoxy)phenyl]propanoate;
13. methyl 3-(4-{3-[4-(acetylmethylamino)phenyl]propyl}-3-methoxyphenyl)propanoate;
14. 3-(4-{3-[4-(butane-1-sulfonyloxy)phenyl]propyl}-3-hydroxyphenyl)propanoic acid;
15. 3-(4-{3-[4-(butane-1-sulfonylamino)phenyl]propyl}-3-butoxyphenyl)propanoic acid;
16. 3-[4-(2-{4-[(3-chlorobenzoyl)methylamino]phenyl}ethoxy)-3-(2-ethoxyethoxy)phenyl]propanoic acid;
17. 3-[3-butoxy-4-(2-{4-[methyl(2-p-tolylethanesulfonyl)amino]phenyl}ethoxy)phenyl]propanoic acid;
18. 3-(4-{3-[4-(butane-1-sulfonyloxy)-3-methoxyphenyl]propyl}-3-butoxyphenyl)propanoic acid;
19. methyl 3-{3-butoxy-4-[3-(4-ethoxy-3-fluoro-phenyl)propyl]phenyl}propanoate;
20. 3-[4-{3-[4-(butane-1-sulfonyloxy)-2-methoxyphenyl]propyl}-3-(2-ethoxyethoxy)phenyl]propanoic acid;
21. 3-(4-{3-[3-chloro-4-(hexane-1-sulfonyloxy)phenyl]propyl}-3-ethoxyphenyl)propanoic acid;
22. 3-{-4-[2-(3-chloro-4-ethoxyphenyl)ethoxy]-3-methoxyphenyl}propanoic acid; and
23. 4-{3-[4-(2-carboxyethyl)-2-methoxyphenyl]propyl}phenyl butyrate.

According to the present invention, the preferred compounds corresponding to the general formula (I) are those that have at least one of the following characteristics:

$R_1$ is a hydroxyl radical,
$R_2$ is an alkyl radical or a polyether radical,
$R_3$ is a hydrogen atom, an alkoxy radical or a halogen,
$R_4$ is an alkyl radical,
X is an oxygen atom or a group $CH_2$,
Y is a sequence $-NR_5SO_2$ or a sequence $-OSO_2$, $R_5$ being as defined previously.

According to the present invention, the compounds most particularly preferred corresponding to the general formula (I) are those that have at least one of the following characteristics:
$R_1$ is a hydroxyl radical,
$R_2$ is a lower alkyl radical,
$R_3$ is a lower alkoxy radical,
$R_4$ is a lower alkyl radical,
X is an oxygen atom or a group $CH_2$,
Y is a sequence $-OSO_2$.

A general description of the methods for preparing the compounds of general formula (I) is given below, with reference to the schemes in FIGS. 1, 2, 3 and 4. In these schemes and in the description of the process that follows, unless otherwise specified, all the substituents are as defined for the compounds of formula (I).

BRIEF DESCRIPTION OF THE DRAWINGS

As presented in FIG. 1, the compounds of general formula (I) for which $X=CH_2$ may be obtained from the intermediates of general formula (5):

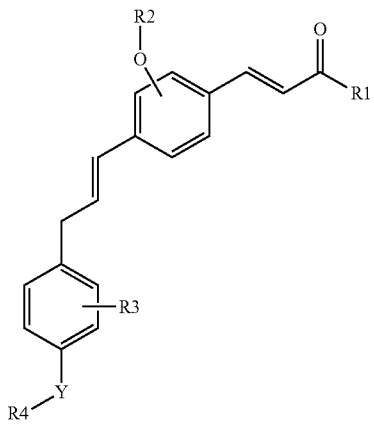

The intermediates of general formula (5) may be prepared via a Heck reaction from the compounds of general formula (2):

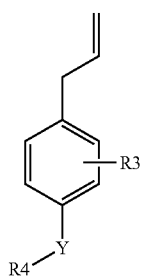

and the iodo compounds of general formula (4)

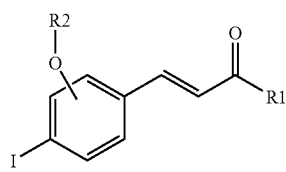

in the presence of a palladium catalyst, for example palladium (II) acetate, and a phosphine.

The compounds of general formula (2) may be obtained from the compounds of general formula (1):

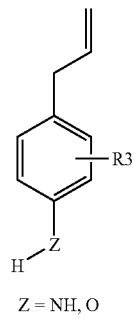

Z = NH, O according to the following steps:
a) either an addition to a sulfonyl chloride ($R_4SO_2Cl$)
b) or an addition to a carboxylic acid halide (for example $R_4COCl$)
c) or a reaction with a halo derivative (for example $R_4Br$ or $R_4Cl$)

in the presence of a base such as sodium hydride or potassium carbonate.

The derivatives thus obtained may optionally be alkylated by reaction with a halo derivative (for example $R_5Br$ or $R_5Cl$) in the presence of a base such as sodium hydride or potassium carbonate.

The process leading to the compounds of general formula (4) from commercial 3-hydroxy-4-iodobenzaldehyde or 2-hydroxy-4-iodobenzaldehyde includes the following two steps:
a) alkylation of 3-hydroxy-4-iodobenzaldehyde or 2-hydroxy-4-iodobenzaldehyde in the presence of a base (for example potassium carbonate) and a halo derivative (for example $R_2Br$ or $R_2Cl$) to give the aldehyde derivatives (3).

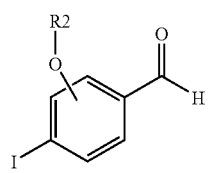

b) a Wittig or Horner-Emmons reaction from the aldehyde precursors thereof (3) and the phosphonates (for example ethyl (diethoxyphosphoryl)acetate) or corresponding phosphoniums (for example methyl (triphenylphosphonium)acetate chloride) to give the compounds of general formula (4).

After reduction of the double bonds of the compounds of general formula (5), compounds (6) are obtained:

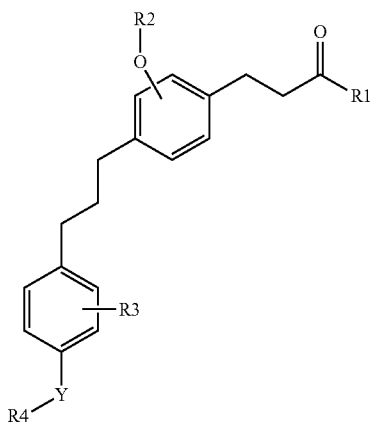
(6)

and then saponified, for example in the presence of sodium hydroxide, in a mixture of tetrahydrofuran and water or of acetone and water, to give the compounds of general formula (7).

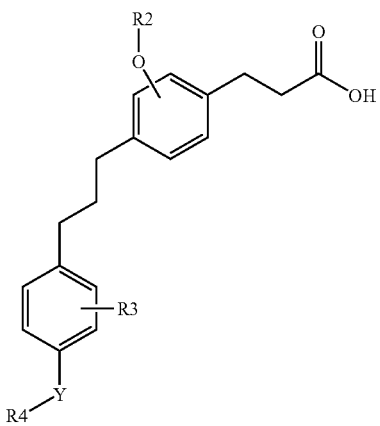
(7)

Figure 2:
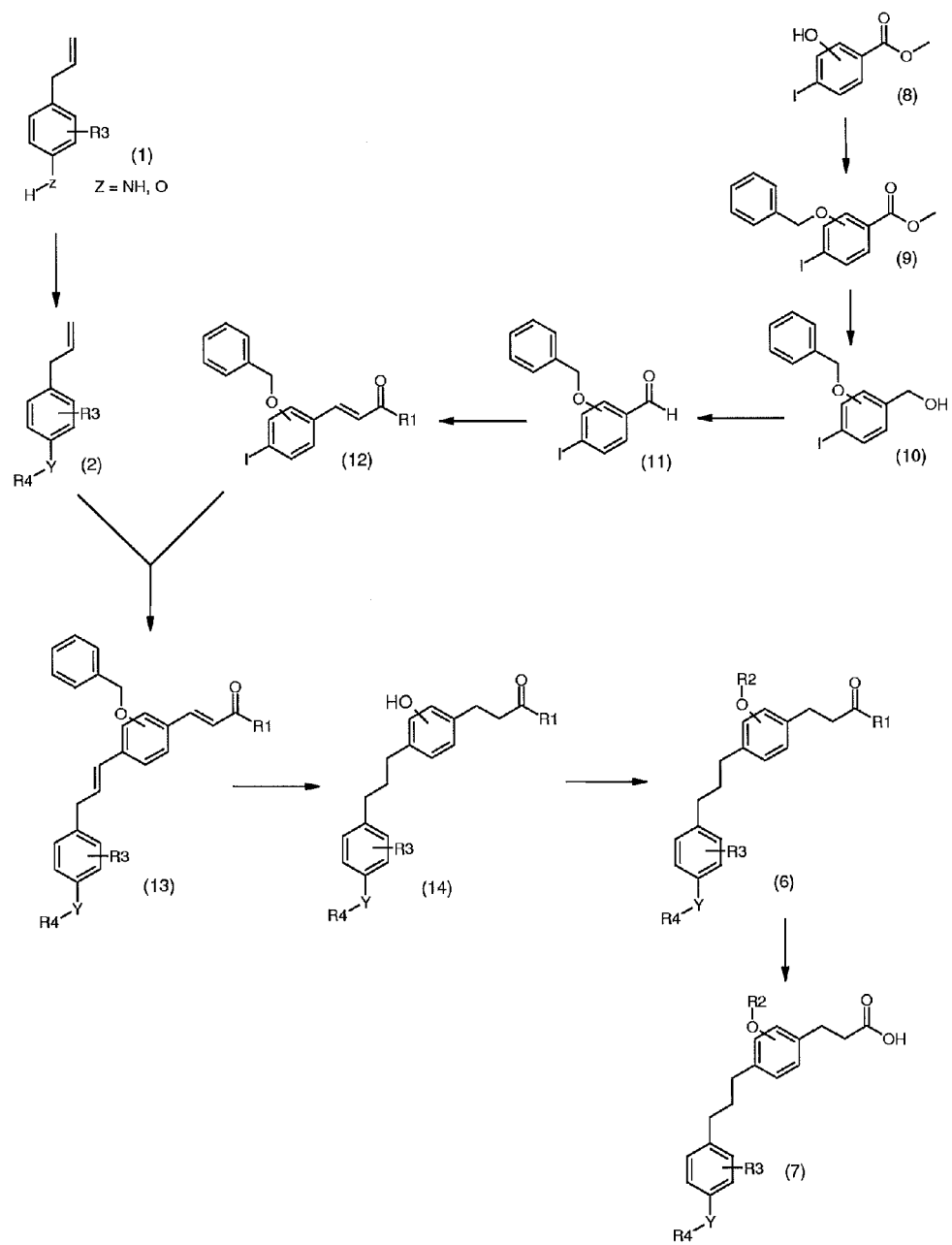

The scheme of FIG. 2 describes another method for obtaining the compounds of general formula (6).

Figure 1:
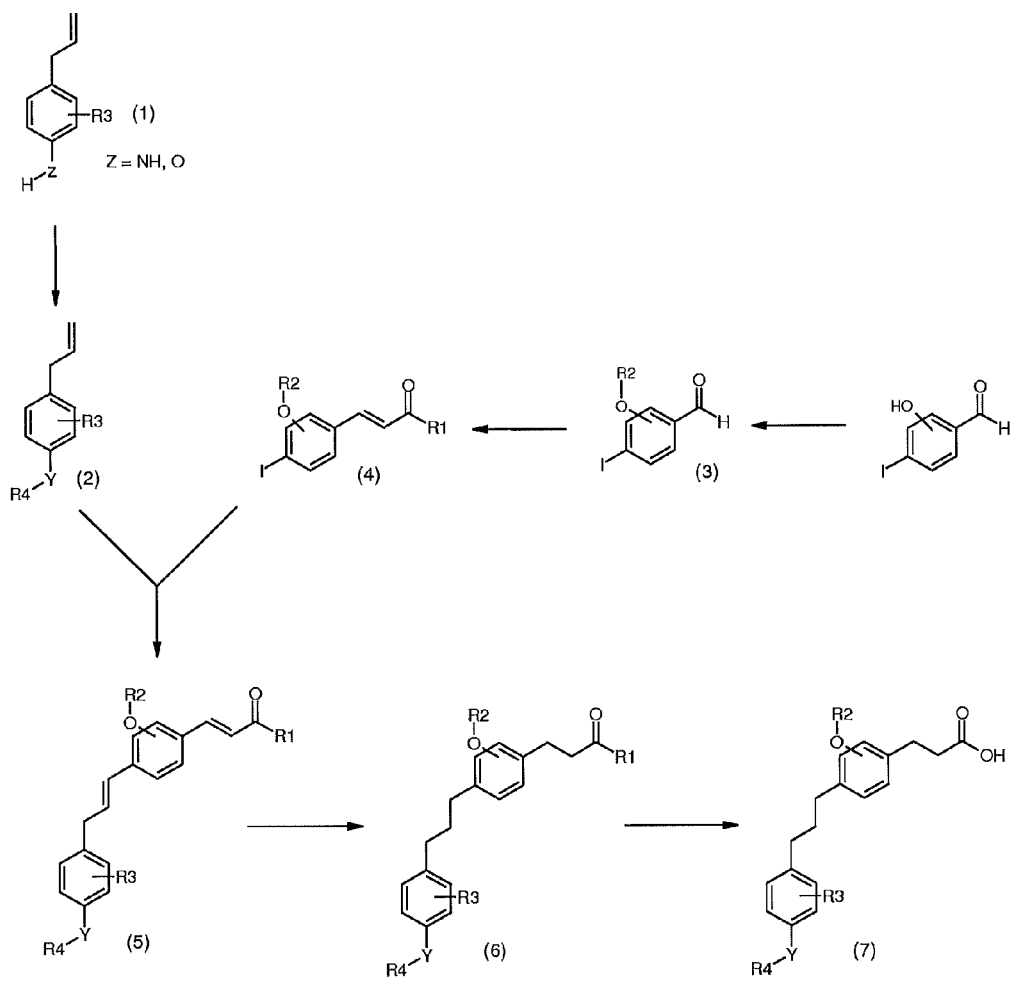

Via a Heck reaction from the derivatives (2) and the iodo derivatives (12) (corresponding to the compounds (4) of FIG. 1 for which $R_2$ is a benzyl),

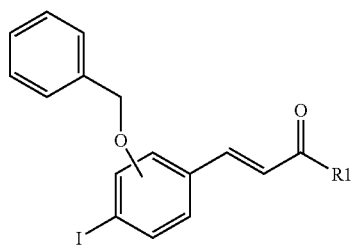
(12)

in the presence of a palladium catalyst, for example palladium (II) acetate, and a phosphine, the compounds of general formula (13) are obtained.

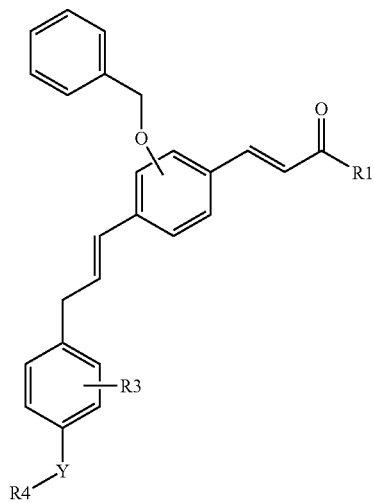
(13)

After reduction of the double bonds and deprotection of the phenol (cleavage of the benzyl ether), the compounds of general formula (14) are obtained.

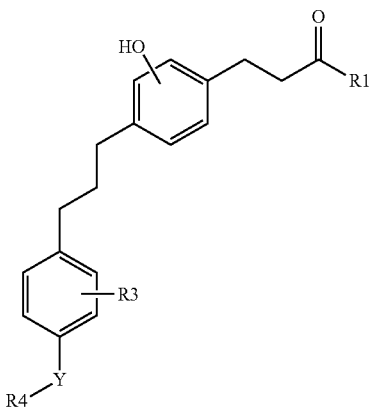
(14)

Via an alkylation reaction of the compounds of general formula (14) with a halo derivative ($R_2Br$ or $R_2I$) in the presence of a base, for instance sodium hydride or potassium carbonate, the compounds of general formula (6) are obtained.

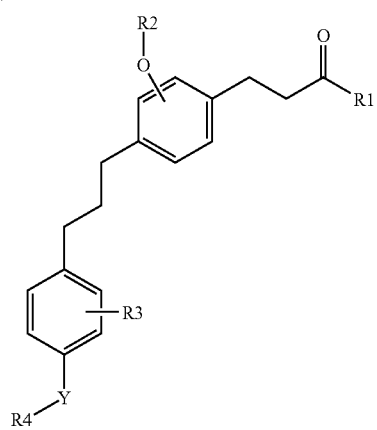
(6)

Figure 3:
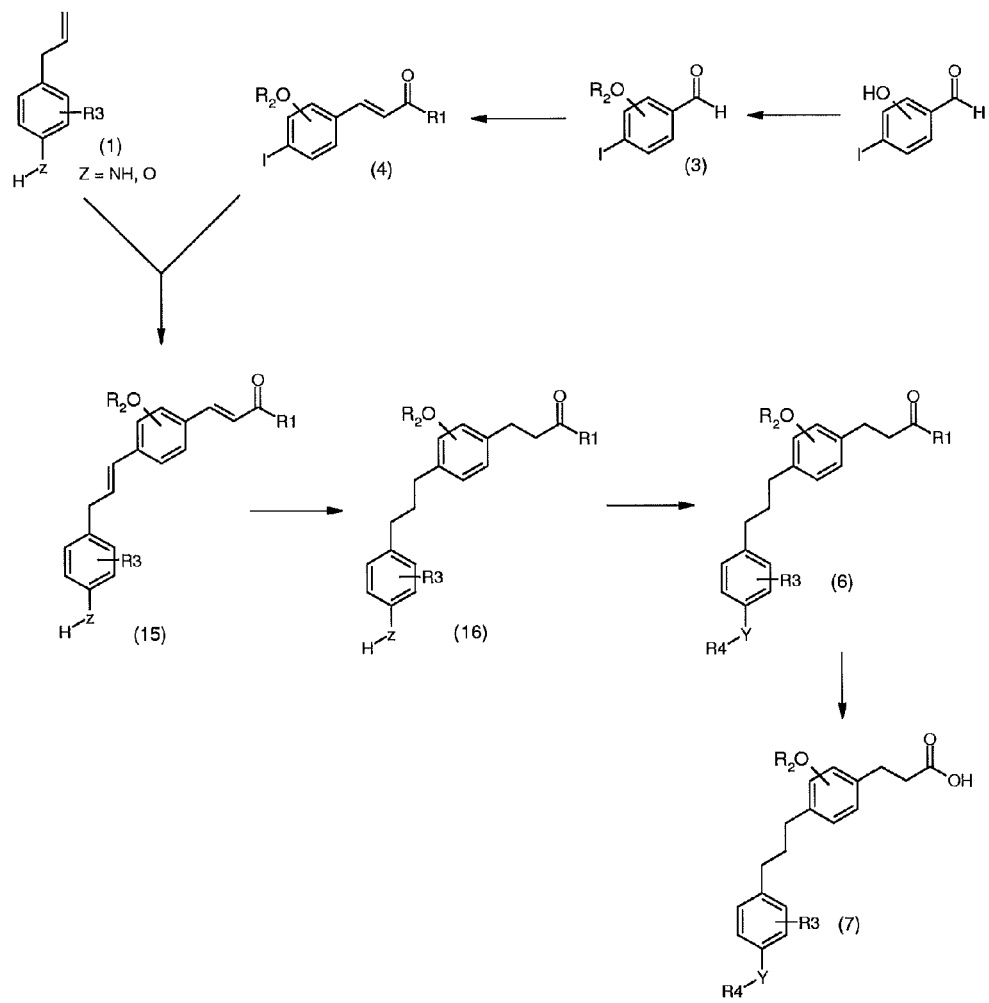

A third method for obtaining the compounds of general formula (6) is described in FIG. 3, starting with a Heck reaction from the 4-allylphenylamine or 4-allylphenol derivative of general formula (1) optionally substituted with a group $R_3$

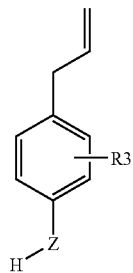

Z = NH, O and an iodo derivative of general formula (4) to give the compound of general formula (15).

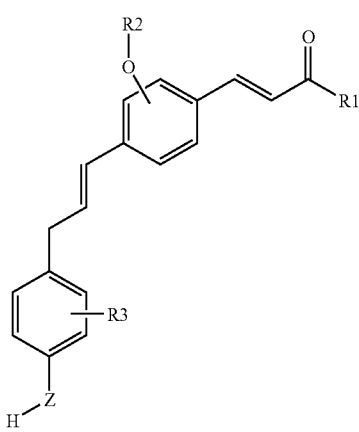

After reduction of the double bonds to give the compounds of general formula (16)

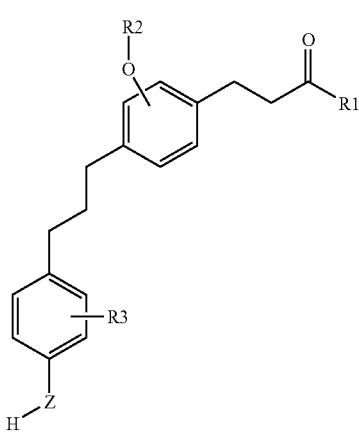

the process leading to the compounds of general formula (6) includes the following steps:

a) either an addition to a sulfonyl chloride ($R_4SO_2Cl$)

b) or an addition to a carboxylic acid halide (for example $R_4COCl$)

c) or a reaction with a halo derivative (for example $R_4Br$ or $R_4Cl$)

in the presence of a base, for instance sodium hydride or potassium carbonate.

The derivatives thus obtained may be optionally alkylated via reaction with a halo derivative (for example $R_5Br$ or $R_5Cl$) in the presence of a base such as sodium hydride or potassium carbonate.

Figure 4:
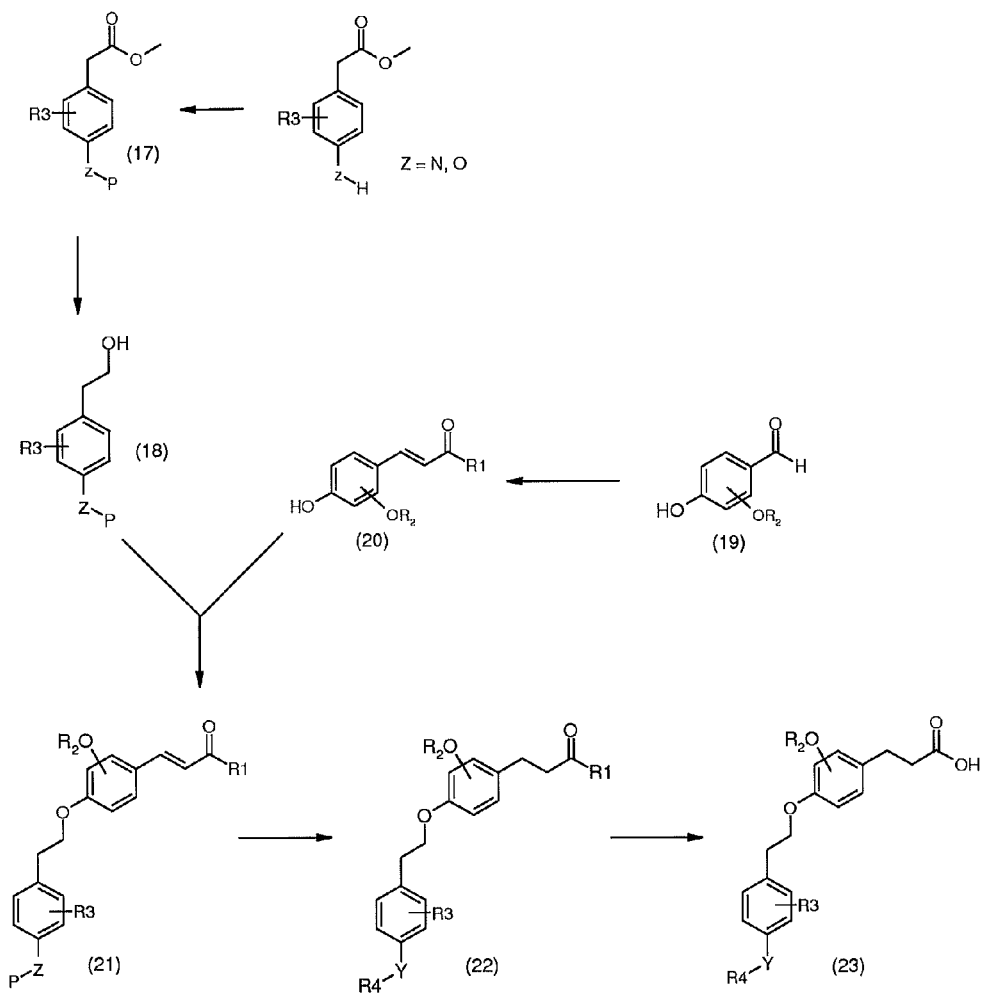

A general description for the preparation of the compounds of formula (I) for which X=O is illustrated in FIG. 4 and detailed below:

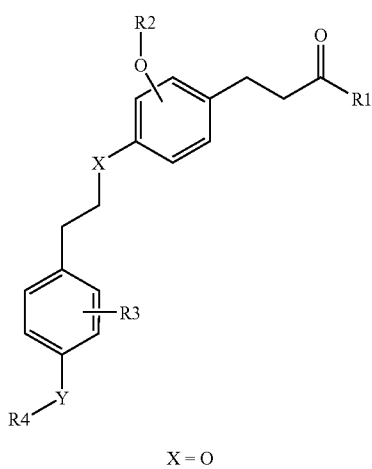

X = O

As shown in FIG. 4, the compounds of general formula (I) for which X=O may be obtained from the intermediates of general formula (21):

(21)

The production of the derivatives of general formula (21) may be performed via a Mitsunobu reaction from the compounds of general formula (18)

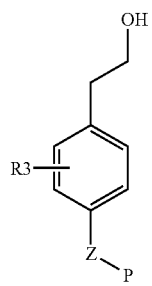

and the compounds of general formula (20)

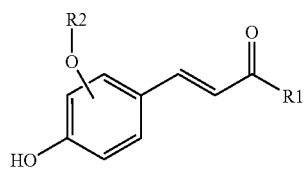

for example in the presence of triphenylphosphine and diethyl azodicarboxylate.

The process for synthesizing the compounds of general formula (18) from commercial derivatives of methyl (4-aminophenyl)acetate or methyl (4-hydroxyphenyl)acetate type optionally substituted with a group $R_3$ includes the following steps:

a) protection of the amine or hydroxyl function to give the compounds of general formula (17)

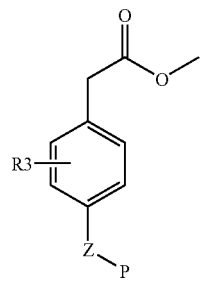

b) reduction of the ester function to an alcohol in the presence of a reducing agent, for instance lithium borohydride.

The compounds of general formula (20) may be obtained via a Wittig or Horner-Emmons reaction from the aldehyde precursors thereof of general formula (19) (prepared beforehand by reacting sodium butoxide with commercial 3-bromo-4-hydroxybenzaldehyde or 2-bromo-4-hydroxybenzaldehyde in the presence of copper (I) chloride) and the phosphonates (for example ethyl(diethoxyphosphoryl)acetate or phosphoniums (for example methyl(triphenylphosphonium)acetate chloride).

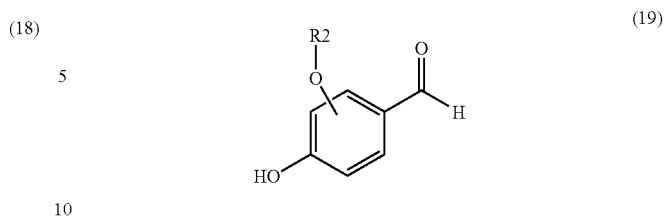

The process leading from the compounds of general formula (21) to the compounds of general formula (23) includes the following steps:

a) deprotection of the alcohol or amine function b) or an addition to a sulfonyl chloride ($R_4SO_2Cl$)

or an addition to a carboxylic acid halide (for example $R_4COCl$)

or a reaction with a halo derivative (for example $R_4Br$ or $R_4Cl$) in the presence of a base, for instance sodium hydride or potassium carbonate.

The derivatives thus obtained may be optionally alkylated via reaction with a halo derivative (for example $R_5Br$ or $R_5Cl$) in the presence of a base such as sodium hydride or potassium carbonate.

c) reduction of the double bond to give the compounds of general formula (22), d) saponification, for example in the presence of sodium hydroxide, in a mixture of tetrahydrofuran and water or acetone and water, to give the compounds of general formula (23).

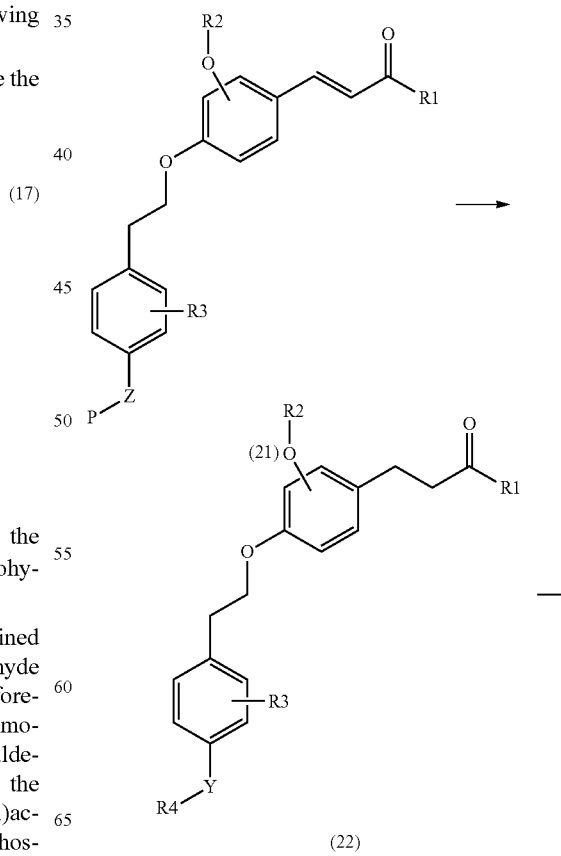

-continued

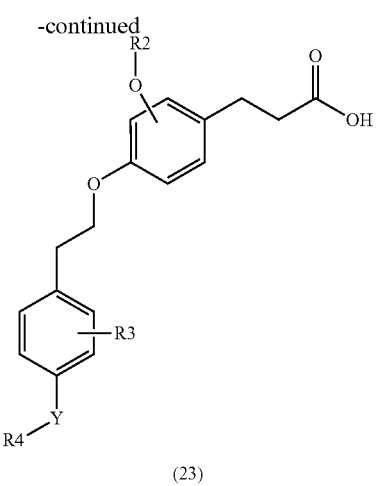

(23)

The functional groups that may be present in the reaction intermediates used in the process may be protected, either in permanent form or in temporary form, with protecting groups that ensure an unequivocal synthesis of the expected compounds. The protection and deprotection reactions are performed according to techniques that are well known to those skilled in the art. The term "temporary protecting group for amines, alcohols or carboxylic acids" means protecting groups such as those described in "Protective Groups in Organic Chemistry", published by McOmie J. W. F., Plenum Press, 1973, in "Protective Groups in Organic Synthesis", 2nd edition, Greene T. W. and Wuts P. G. M., published by John Wiley and Sons, 1991 and in "Protecting Groups", Kocienski P. J., 1994, Georg Thieme Verlag.

The compounds according to the invention show modulatory properties on receptors of PPAR type. This activity on the PPARα, δ and γ receptors is measured in a transactivation test and quantified by the dissociation constant Kdapp (apparent), as described in Example 10.

The preferred compounds of the present invention have a dissociation constant of less than or equal to 1000 nM and advantageously less than or equal to 200 nM.

Preferably, the compounds are specific PPARγ type receptor modulators, i.e. they have a ratio from the Kdapp for the PPARα or PPARδ receptors and the Kdapp for the PPARγ receptors, of greater than or equal to 10. Preferably, this PPARα/PPARγ or PPARδ/PPARγ ratio is greater than or equal to 50 and more advantageously greater than or equal to 100.

The present invention also features, as medicaments, the compounds of formula (I) as described above.

Thus, the compounds as described above according to the invention may be formulated into compositions for regulating and/or restoring skin lipid metabolism.

The present invention also features medicaments comprising the compounds of formula (i) and administration thereof in the treatment and/or prevention of the disorders described below.

The compounds according to the invention are particularly suitable in the following fields of treatment; whether regime or regimen:

1) for treating dermatological complaints or conditions associated with a keratinization disorder relating to cell differentiation and proliferation, especially for treating common acne, comedones, polymorphs, acne rosacea, nodulocystic acne, acne conglobata, senile acne, and secondary acnes such as solar acne, medication-related acne or occupational acne;

2) for treating other types of keratinization disorders, especially ichthyosis, ichthyosiform conditions, Darier's disease, palmoplantar keratoderma, leukoplakia and leukoplakiform conditions, and cutaneous or mucous (buccal) lichen;

3) for treating other dermatological complaints or conditions with an inflammatory immunoallergic component, with or without cell proliferation disorder, and especially all forms of psoriasis, whether cutaneous, mucous or ungual, and even psoriatic rheumatism, or cutaneous atopy, such as eczema, or respiratory atopy, or alternatively gingival hypertrophy;

4) for treating all dermal or epidermal proliferations, whether benign or malignant, and whether of viral origin or otherwise, such as common warts, flat warts and verruciform epidermodysplasia, oral or florid papillomatoses, T lymphoma, and proliferations that may be induced by ultraviolet radiation, especially in the case of basal cell and spinal cell epithelioma, and also any precancerous skin lesion such as keratoacanthomas;

5) for treating other dermatological disorders such as immune dermatoses, such as lupus erythematosus, immune bullous diseases and collagen diseases, such as scleroderma;

6) in the treatment of dermatological or general complaints or conditions with an immunological component;

7) in the treatment of skin disorders caused by exposure to UV radiation, and also for repairing or combating aging of the skin, whether photoinduced or chronological aging, or for reducing actinic pigmentations and keratosis, or any pathology associated with chronological or actinic ageing, such as xerosis;

8) for combating sebaceous function disorders, such as the hyperseborrhoea of acne or simple seborrhoea;

9) for preventing or treating cicatrization disorders, or for preventing or repairing stretchmarks;

10) in the treatment of pigmentation disorders, such as hyperpigmentation, melasma, hypopigmentation or vitiligo;

11) in the treatment of lipid metabolism complaints, such as obesity, hyperlipidaemia, or non-insulin-dependent diabetes;

12) in the treatment of inflammatory complaints or conditions such as arthritis;

13) in the treatment or prevention of cancerous or precancerous conditions;

14) in the prevention or treatment of alopecia of various origins, especially alopecia caused by chemotherapy or radiation;

15) in the treatment of disorders of the immune system, such as asthma, type I sugar diabetes, multiple sclerosis or other selective dysfunctions of the immune system; and 16) in the treatment of complaints or conditions of the cardiovascular system, such as arteriosclerosis or hypertension.

The present invention also features pharmaceutical or cosmetic compositions comprising, formulated into a physiologically acceptable medium, at least one compound of formula (I) as defined above.

The term "physiologically acceptable medium" means a medium that is compatible with the skin, mucous membranes and the integuments.

The present invention also features formulation of the compounds of formula (I) into medicaments for treating the above-mentioned complaints and conditions, in particular for regulating and/or restoring skin lipid metabolism.

The compositions according to the invention may be administered orally, enterally, parenterally, topically or ocularly. The pharmaceutical composition is preferably packaged in a form that is suitable for topical application. The term "topical route" means administration to the skin and/or the integuments.

Via the oral route, the composition, more particularly the pharmaceutical composition, may be in the form of tablets, gel capsules, dragees, syrups, suspensions, solutions, powders, granules, emulsions, lipid or polymeric microspheres, nanospheres or vesicles allowing a controlled release. Via the parenteral route, the composition may be in the form of solutions or suspensions for infusion or for injection.

The compounds according to the invention are generally administered at a daily dose of about 0.001 mg/kg to 100 mg/kg of body weight, in 1 to 3 dosage intakes.

The compounds are administered systemically, at a concentration generally of from 0.001% to 10% by weight and preferably from 0.01% to 1% by weight, relative to the weight of the composition.

Via the topical route, the pharmaceutical composition according to the invention is more particularly intended for treating the skin and mucous membranes and may be in the form of ointments, creams, milks, pomades, powders, impregnated pads, solutions, gels, sprays, lotions or suspensions. It may also be in the form of lipid or polymeric microspheres, nanospheres or vesicles or polymer patches and hydrogels allowing a controlled release. This topical composition may be in anhydrous form, in aqueous form or in the form of an emulsion.

The compounds are administered topically at a concentration generally of from 0.001% to 10% by weight and preferably from 0.01% to 1% by weight, relative to the total weight of the composition.

The compounds of formula (I) according to the invention also find application in cosmetics, in particular in body and hair hygiene and more particularly for regulating and/or restoring skin lipid metabolism.

The present invention thus also features the cosmetic use of a composition comprising, in a physiologically acceptable support, at least one of the compounds of formula (I) for body or hair hygiene.

The cosmetic compositions according to the invention containing, in a cosmetically acceptable support, at least one compound of formula (I) or an optical or geometrical isomer thereof or a salt thereof, may especially be in the form of a cream, a milk, a lotion, a gel, lipid or polymeric microspheres, nanospheres or vesicles, a soap or a shampoo.

The concentration of compound of formula (I) in the cosmetic composition is from 0.001% to 3% by weight relative to the total weight of the composition.

The compositions as described above may also obviously contain inert or even pharmacodynamically active additives or combinations of these additives, and especially: wetting agents, depigmenting agents such as hydroquinone, azelaic acid, caffeic acid or kojic acid; emollients; moisturizers, for instance glycerol, PEG-400, thiamorpholinone and derivatives thereof, or alternatively urea; anti-seborrhoeic or anti-acne agents, such as S-carboxymethylcysteine or S-benzylcysteamine, and salts or derivatives thereof, or benzoyl peroxide; antifungal agents such as ketoconazole or 4,5-polymethylene-3-isothiazolidones; antibacterial agents, carotenoids and especially β-carotene; anti-psoriatic agents such as anthralin and derivatives thereof; eicosa-5,8,11,14-tetraynoic and eicosa-5,8,11-triynoic acids, esters and amides thereof, and, finally, retinoids. The compounds of formula (I) may also be combined with D vitamins or derivatives thereof, with corticosteroids, with free-radical scavengers, α-hydroxy or α-keto acids or derivatives thereof, or alternatively with ion-channel blockers.

These compositions may also contain flavor enhancers, preservatives such as para-hydroxybenzoic acid esters, stabilizers, moisture regulators, pH regulators, osmotic pressure modifiers, emulsifiers, UV-A and UV-B screening agents, and antioxidants such as α-tocopherol, butylhydroxyanisole or butylhydroxytoluene.

Needless to say, one skilled in the art will take care to select the optional compound(s) to be added to these compositions such that the advantageous properties intrinsically associated with the present invention are not, or are not substantially, adversely affected by the envisaged addition.

In order to further illustrate the present invention and the advantages thereof, the following specific examples are given, including results of biological activity, it being understood that same are intended only as illustrative and in nowise limitative. In said examples to follow, all parts and percentages are given by weight, unless otherwise indicated.

Example 1

3-{4-[3-(4-benzyloxy-3-methoxyphenyl)propyl]-3-butoxyphenyl}propanoic acid a—3-butoxy-4-iodobenzaldehyde 21.5 ml (189 mmol) of 1-iodobutane are added to a solution of 31 g (126 mmol) of 3-hydroxy-4-iodobenzaldehyde in 350 ml of methyl ethyl ketone in the presence of 52.2 g (378 mmol) of potassium carbonate. The reaction medium is heated at 85° C. for 2 hours. The solid is filtered off and the solvent is evaporated off. The solid obtained is washed with heptane and 38 g (99%) of 3-butoxy-4-iodobenzaldehyde are obtained in the form of white crystals.

b—methyl(E)-3-(3-butoxy-4-iodophenyl)acrylate 65.1 g (195 mmol) of methyl (triphenylphosphoranylidene)acetate are added to a solution of 29.6 g (97 mmol) of 3-butoxy-4-iodobenzaldehyde in 360 ml of toluene. The reaction mixture is refluxed for 2 hours. The solvent is evaporated off and the oil obtained is purified by chromatography on a column of silica eluted with a 50/50 heptane/dichloromethane mixture. 30.5 g (87%) of methyl(E)-3-(3-butoxy-4-iodophenyl)acrylate are obtained in the form of pale yellow crystals.

c—methyl(E)-3-{3-butoxy-4-[(E)-3-(4-hydroxy-3-methoxyphenyl)propenyl]phenyl}acrylate A solution of 1.1 g (12.1 mmol) of eugenol, 2.0 g (5.5 mmol) of methyl(E)-3-(3-butoxy-4-iodophenyl)acrylate, 24 mg (0.1 mmol) of palladium (II) acetate and 77 mg (0.2 mmol) of 2-(dicyclohexylphosphino)biphenyl in 15 ml of a 6/1 dimethylformamide/triethylamine mixture is stirred at 90° C. for 3 hours. After addition of water, the reaction medium is extracted with ethyl acetate. The organic phases are washed with saturated aqueous sodium chloride solution, dried over sodium sulfate, filtered and evaporated. The residual oil is purified by chromatography on a column of silica eluted with an 8/2 heptane/ethyl acetate mixture.

d—methyl 3-{3-butoxy-4-[3-(4-hydroxy-3-methoxyphenyl)propyl]phenyl}propanoate 500 mg of Pd/C are added to a solution of methyl(E)-3-{3-butoxy-4-[(E)-3-(4-hydroxy-3-methoxyphenyl)propenyl]phenyl}acrylate in 25 ml of methanol. The reaction medium is stirred under a hydrogen atmosphere at room temperature for 3 hours. After filtering off the catalyst and evaporating off the solvent, 2.0 g (90%) of methyl 3-{3-butoxy-4-[3-(4-hydroxy-3-methoxyphenyl)propyl]phenyl}propanoate are obtained in the form of a colorless oil.

e—methyl 3-{4-[3-(4-benzyloxy-3-methoxyphenyl) propyl]-3-butoxyphenyl}propanoate 0.2 g (0.75 mmol) of potassium carbonate and then 0.2 ml (0.75 mmol) of benzyl bromide are added to a solution of 0.25 g (0.62 mmol) of methyl 3-{3-butoxy-4-[3-(4-hydroxy-3-methoxyphenyl)propyl]phenyl}propanoate in 25 ml of methyl ethyl ketone. The reaction mixture is heated at 70° C. for 24 hours and then cooled, diluted with ethyl acetate and washed with saturated aqueous sodium chloride solution. The organic phase is dried over sodium sulfate, filtered and evaporated. The residue obtained is purified by chromatography on a column of silica eluted with an 80/20 heptane/ethyl acetate mixture. 276 mg (93%) of methyl 3-{4-[3-(4-benzyloxy-3-methoxyphenyl)propyl]-3-butoxyphenyl}propanoate are obtained in the form of a colorless oil.

f—3-{4-[3-(4-benzyloxy-3-methoxyphenyl)propyl]-3-butoxyphenyl}propanoic acid 0.84 ml (0.84 mmol) of aqueous 1N lithium hydroxide solution is added to a solution of 276 mg (0.56 mmol) of methyl 3-{4-[3-(4-benzyloxy-3-methoxyphenyl)propyl]-3-butoxyphenyl}propanoate in 3 ml of tetrahydrofuran. The reaction mixture is stirred at room temperature for 12 hours. The reaction medium is evaporated to dryness and the residue is then taken up in water and the medium is acidified by addition of acetic acid solution and then extracted with ethyl acetate. The organic phases are combined, washed with saturated aqueous sodium chloride solution, dried over magnesium sulfate, filtered and evaporated. After recrystallization from cyclohexane and filtration, 205 mg (77%) of 3-{4-[3-(4-benzyloxy-3-methoxyphenyl)propyl]-3-butoxyphenyl}propanoic acid are obtained in the form of white crystals with a melting point of 92° C.

NMR ($^1$H, CDCl$_3$): 0.97 (t, J=7.4 Hz, 3H); 1.48 (m, 2H); 1.75 (m, 2H); 1.87 (m, 2H); 2.59 (q, 2H); 2.67 (t, J=8.1 Hz, 2H); 2.92 (t, J=8.1 Hz, 2H); 3.88 (s, 3H); 3.93 (t, J=6.3 Hz, 2H); 5.12 (s, 2H); 6.65-6.70 (m, 2H); 6.73 (d, J=6.3 Hz, 1H); 7.02 (d, J=7.5 Hz); 7.28-7.44 (m, 5H).

Example 2

3-{3-butoxy-4-[3-(4-ethoxy-3-methoxyphenyl)propyl]phenyl}propanoic acid a—methyl 3-{4-[3-(4-ethoxy-3-methoxyphenyl) propyl]-3-butoxyphenyl}propanoate 0.21 g (0.75 mmol) of potassium carbonate and then 0.12 ml (0.75 mmol) of iodoethane are added to a solution of 0.25 g (0.62 mmol) of methyl 3-{3-butoxy-4-[3-(4-hydroxy-3-methoxyphenyl)propyl]phenyl}propanoate (prepared according to Example 1d) in 25 ml of methyl ethyl ketone. The reaction mixture is heated at 70° C. for 24 hours. The reaction medium is cooled, diluted with ethyl acetate and washed with saturated aqueous sodium chloride solution. The organic phase is dried over sodium sulfate, filtered and evaporated and the residue is then purified by chromatography on a column of silica eluted with an 80/20 heptane/ethyl acetate mixture. 240 mg (93%) of ethyl 3-{4-[3-(4-ethoxy-3-methoxyphenyl)propyl]-3-butoxyphenyl}propanoate are obtained in the form of a colorless oil.

b—3-{3-butoxy-4-[3-(4-ethoxy-3-methoxyphenyl) propyl]phenyl}propanoic acid ml (1.1 mmol) of aqueous 1N lithium hydroxide solution are added to a solution of 240 mg (0.56 mmol) of methyl 3-{3-butoxy-4-[3-(4-ethoxy-3-methoxyphenyl)propyl]phenyl}propanoate in 3 ml of tetrahydrofuran. The reaction mixture is stirred at room temperature for 12 hours. The reaction medium is concentrated and then taken up in water and acidified by addition of aqueous hydrochloric acid solution and then extracted with ethyl acetate. The organic phases are combined, washed with saturated aqueous sodium chloride solution and then dried over magnesium sulfate and filtered. The solvents are evaporated off. After recrystallization of the residue obtained from 6 ml of cyclohexane, 184 mg (79%) of 3-{3-butoxy-4-[3-(4-ethoxy-3-methoxyphenyl)propyl]phenyl}propanoic acid are obtained in the form of a white solid with a melting point of 66° C.

NMR ($^1$H, CDCl$_3$): 0.97 (t, J=7.4 Hz, 3H); 1.44 (t, J=7 Hz, 3H); 1.49 (m, 2H); 1.75 (m, 2H); 1.88 (m, 2H); 2.58-2.69 (m, 6H); 2.92 (t, J=7.6 Hz, 2H); 3.85 (s, 3H); 3.94 (t, J=6.3 Hz, 2H); 4.07 (q, J=7 Hz, 2H); 6.67-6.71 (m, 4H); 6.78 (m, 1H); 7.03 (d, J=7.5 Hz).

Example 3

3-{3-butoxy-4-[3-(4-butoxy-3-methoxyphenyl)propyl]phenyl}propanoic acid a—methyl 3-{4-[3-(4-butoxy-3-methoxyphenyl) propyl]-3-propoxyphenyl}propanoate 0.21 g (0.75 mmol) of potassium carbonate and then 0.85 ml (0.75 mmol) of benzyl bromide are added to a solution of 0.25 g (0.62 mmol) of methyl 3-{3-butoxy-4-[3-(4-hydroxy-3-methoxyphenyl)propyl]phenyl}propanoate (prepared according to Example 1d) in 25 ml of methyl ethyl ketone. The reaction mixture is heated at 70° C. for 24 hours and then cooled, diluted with ethyl acetate and washed with saturated aqueous sodium chloride solution. The organic phase is dried over sodium sulfate, filtered and evaporated. The residue is purified by chromatography on a column of silica eluted with an 80/20 heptane/ethyl acetate mixture. 259 mg (93%) of methyl 3-{4-[3-(4-butoxy-3-methoxyphenyl)propyl]-3-propoxyphenyl}propanoate are obtained in the form of a colorless oil.

b—3-{3-butoxy-4-[3-(4-butoxy-3-methoxyphenyl) propyl]phenyl}propanoic acid 1.14 ml (0.85 mmol) of aqueous 1N lithium hydroxide solution are added to a solution of 259 mg (0.56 mmol) of methyl 3-{3-butoxy-4-[3-(4-butoxy-3-methoxyphenyl)propyl]phenyl}propanoate in 3 ml of tetrahydrofuran. The reaction mixture is stirred at room temperature for 12 hours and then concentrated under vacuum. The residue is taken up in water, acidified by adding 1N hydrochloric acid solution and then extracted with ethyl acetate. The organic phases are combined, washed with saturated aqueous sodium chloride solution, dried over magnesium sulfate, filtered and evaporated. After trituration in heptane, 208 mg (83%) of 3-{3-butoxy-4-[3-(4-butoxy-3-methoxyphenyl)propyl]

phenyl}propanoic acid are obtained in the form of white crystals with a melting point of 64° C.

NMR ($^1$H, CDCl$_3$): 0.96 (t, J=7.4 Hz, 3H); 0.98 (t, J=7.5 Hz, 3H); 1.45-1.51 (m, 4H); 1.74-1.88 (m, 6H); 2.57-2.69 (m, 6H); 2.92 (t, J=7.6 Hz, 2H); 3.84 (s, 3H); 3.93 (t, J=6.3 Hz, 2H); 3.99 (t, J=6.8 Hz, 2H); 6.67-6.71 (m, 4H); 6.79 (m, 1H); 7.03 (d, J=7.5 Hz, 1H).

Example 4

3-{3-butoxy-4-[3-(4-methanesulfonyloxy-3-methoxyphenyl)propyl]phenyl}propanoic acid a—4-allyl-2-methoxyphenyl methanesulfonate 3.1 ml (40 mmol) of methanesulfonyl chloride are added to a solution of 6 g (36 mmol) of eugenol and 5.5 ml (43 mmol) of triethylamine in 100 ml of dichloromethane, cooled beforehand to −20° C. After stirring at room temperature for 3 hours, the reaction medium is treated with water and ethyl acetate. The organic phase is dried over magnesium sulfate, filtered and evaporated. 9.5 g (100%) of 4-allyl-2-methoxyphenyl methanesulfonate are obtained.

b—methyl(E)-3-{3-butoxy-4-[(E)-3-(4-methanesulfonyloxy-3-methoxyphenyl)propenyl]phenyl}acrylate A solution of 334 mg (1.4 mmol) of 4-allyl-2-methoxyphenyl methanesulfonate, 500 mg (1.4 mmol) of methyl(E)-3-(3-butoxy-4-iodophenyl)acrylate (prepared according to Example 1b), 15 mg of palladium acetate and 48 mg of 2-(dicyclohexylphosphino)biphenyl in 5 ml of a 6/1 dimethylformamide/triethylamine mixture is stirred for 3 hours at 80° C. After addition of water and extraction with ethyl acetate, the organic phases are washed with saturated aqueous sodium chloride solution and dried over sodium sulfate. The residual oil is purified by chromatography on a column of silica eluted with an 8/2 heptane/ethyl acetate mixture.

c—methyl 3-{3-butoxy-4-[3-(4-methanesulfonyloxy-3-methoxyphenyl)propyl]phenyl}propanoate 100 mg of palladium-on-charcoal are added to a solution of methyl(E)-3-{3-butoxy-4-[(E)-3-(4-methanesulfonyloxy-3-methoxyphenyl)propenyl]phenyl}acrylate obtained previously in 10 ml of methanol. The reaction medium is stirred for one hour at room temperature under a hydrogen atmosphere. After filtering off the catalyst on Celite and evaporating off the solvent, 600 mg (91% for the two steps) of methyl 3-{3-butoxy-4-[3-(4-methanesulfonyloxy-3-methoxyphenyl)propyl]phenyl}propanoate are obtained in the form of a colorless oil.

d—3-{3-butoxy-4-[3-(4-methanesulfonyloxy-3-methoxyphenyl)propyl]phenyl}propanoic acid 600 mg (1.25 mmol) of methyl 3-{3-butoxy-4-[3-(4-methanesulfonyloxy-3-methoxyphenyl)propyl]phenyl}propanoate are dissolved in 10 ml of tetrahydrofuran and 1.8 ml (1.8 mmol) of aqueous 1N lithium hydroxide solution are then added. The reaction medium is stirred for 15 hours at room temperature. After addition of water and acidification with acetic acid, the reaction medium is extracted with ethyl acetate. The organic phases are combined, dried over sodium sulfate, filtered and evaporated. The residue obtained is purified by chromatography on a column of silica eluted with an 8/2 heptane/ethyl acetate mixture. 480 mg (82%) of 3-{3-butoxy-4-[3-(4-methanesulfonyloxy-3-methoxyphenyl)propyl]phenyl}propanoic acid are obtained after crystallization from a 2/8 isopropyl ether/pentane mixture.

NMR ($^1$H, CDCl$_3$): 0.97 (t, J=7.4 Hz, 3H); 1.48 (m, 2H); 1.75 (m, 2H); 1.90 (m, 2H); 2.61-2.69 (m, 6H); 2.92 (t, J=7.6 Hz, 2H); 3.16 (s, 3H); 3.86 (s, 3H); 3.94 (t, J=6.4 Hz, 2H); 6.78 (s, 1H); 6.70 (d, J=7.6 Hz, 1H); 6.77-6.80 (m, 2H); 7.03 (d, J=7.6 Hz, 1H); 7.19 (d, J=8.6 Hz, 1H).

Example 5

3-(4-{3-[4-(butane-1-sulfonyloxy)-3-methoxyphenyl]propyl}-3-butoxyphenyl)propanoic acid a—methyl(E)-3-{3-butoxy-4-[(E)-3-(4-hydroxy-3-methoxyphenyl)propenyl]phenyl}acrylate A solution of 1.1 g (12.1 mmol) of eugenol, 2.0 g (5.5 mmol) of methyl(E)-3-(3-butoxy-4-iodophenyl)acrylate (prepared according to Example 1b), 24 mg (0.1 mmol) of palladium (II) acetate and 77 mg (0.2 mmol) of 2-(dicyclohexylphosphino)biphenyl in 15 ml of a 6/1 dimethylformamide/triethylamine mixture is stirred at 90° C. for 3 hours. After addition of water, the reaction medium is extracted with ethyl acetate. The organic phases are washed with saturated aqueous sodium chloride solution, dried over sodium sulfate, filtered and evaporated. The residual oil is purified by chromatography on a column of silica eluted with an 8/2 heptane/ ethyl acetate mixture.

b—methyl 3-{3-butoxy-4-[3-(4-hydroxy-3-methoxyphenyl)propyl]phenyl}propanoate 500 mg of palladium-on-charcoal are added to a solution of methyl(E)-3-{3-butoxy-4-[(E)-3-(4-hydroxy-3-methoxyphenyl)propenyl]phenyl}acrylate in 25 ml of methanol. The reaction medium is stirred under a hydrogen atmosphere at room temperature for 3 hours. After filtering off the catalyst and evaporating off the solvent, 2.0 g (90%) of methyl 3-{3-butoxy-4-[3-(4-hydroxy-3-methoxyphenyl)propyl]phenyl}propanoate are obtained in the form of a colorless oil.

c—methyl 3-(4-{3-[4-(butane-1-sulfonyloxy)-3-methoxyphenyl]propyl}-3-butoxyphenyl)propanoate A solution of 400 mg (1 mmol) of methyl 3-{3-butoxy-4-[3-(4-hydroxy-3-methoxyphenyl)propyl]phenyl}propanoate, 170 µl (1.3 mmol) of butanesulfonyl chloride and 250 µl of triethylamine in 10 ml of tetrahydrofuran is stirred for 12 hours at room temperature. After addition of water and extraction with ethyl acetate, the organic phases are washed with saturated aqueous sodium chloride solution, dried over sodium sulfate, filtered and evaporated. The residual oil is purified by chromatography on a column of silica eluted with an 8/2 heptane/ethyl acetate mixture. 410 mg of methyl 3-(4-{3-[4-(butane-1-sulfonyloxy)-3-methoxyphenyl]propyl}-3-butoxyphenyl)propanoate are obtained in the form of a yellow oil.

d—3-(4-{3-[4-(butane-1-sulfonyloxy)-3-methoxyphenyl]propyl}-3-butoxyphenyl)propanoic acid 410 mg of methyl 3-(4-{3-[4-(butane-1-sulfonyloxy)-3-methoxyphenyl]propyl}-3-butoxyphenyl)propanoate are dissolved in 10 ml of tetrahydrofuran, and 1.8 ml of aqueous 1N lithium hydroxide solution are added. The reaction medium is stirred for 15 hours at room temperature. After addition of water and acidification to pH 4 with acetic acid, the reaction medium is extracted with ethyl acetate. The organic phase is dried over sodium sulfate, filtered and evaporated. The residue obtained is purified by chromatography on a column of silica eluted with an 8/2 heptane/ethyl acetate mixture. 136 m g (27% for the two steps) of 3-(4-{3-[4-(butane-1-sulfonyloxy)-3-methoxyphenyl]propyl}-3-butoxyphenyl)propanoic acid are obtained in the form of a colorless oil.

NMR ($^1$H, CDCl$_3$): 0.98 (t, J=7.4 Hz, 3H); 1.01 (t, J=7 Hz, 3H); 1.49-1.54 (m, 4H); 1.77 (m, 2H); 1.91 (m, 2H); 1.99 (m, 2H); 2.63-2.67 (m, 6H); 2.92 (t, J=7.6 Hz, 2H); 3.28 (t, J=6.4 Hz, 2H); 3.70 (s, 3H); 4.14 (m, 2H); 6.69 (s, 1H); 6.71 (d, J=7.5 Hz, 2H); 6.79 (m, 2H); 7.04 (dd, J=2.8 Hz, J=7.4 Hz, 1H); 7.20 (dd, J=1.7 Hz, J=7 Hz, 1H).

Example 6

3-{3-butoxy-4-[3-(4-ethanesulfonyloxy-3-methoxyphenyl)propyl]phenyl}propanoic acid a—methyl 3-{3-butoxy-4-[3-(4-ethanesulfonyloxy-3-methoxyphenyl)propyl]phenyl}propanoate 0.2 ml (1.6 mmol) of triethylamine and then 0.15 ml (1.7 mmol) of ethanesulfonyl chloride are added to a solution of 0.5 g (1.25 mmol) of methyl 3-{3-butoxy-4-[3-(4-hydroxy-3-methoxyphenyl)propyl]phenyl}propanoate (prepared according to Example 1d) in 3 ml of dichloromethane, cooled beforehand to −20° C. The reaction medium is stirred at room temperature for 3 hours and is then treated by addition of saturated aqueous sodium chloride solution and extracted with ethyl acetate. The organic phases are combined, dried over sodium sulfate, filtered and evaporated. The residue is purified by chromatography on a column of silica eluted with a 90/10 heptane/ethyl acetate mixture. 618 mg (99%) of methyl 3-{3-butoxy-4-[3-(4-ethanesulfonyloxy-3-methoxyphenyl)propyl]phenyl}propanoate are obtained in the form of a colorless oil.

b—3-{3-butoxy-4-[3-(4-ethanesulfonyloxy-3-methoxyphenyl)propyl]phenyl}propanoic acid ml (0.85 mmol) of aqueous 1N lithium hydroxide solution are added to a solution of 259 mg (0.6 mmol) of methyl 3-{3-butoxy-4-[3-(4-ethanesulfonyloxy-3-methoxyphenyl)propyl]phenyl}propanoate in 3 ml of tetrahydrofuran. The reaction mixture is stirred at room temperature for 12 hours, concentrated and then taken up in water, acidified by adding hydrochloric acid solution and then extracted with ethyl acetate ethyl. The organic phases are combined, washed with saturated sodium chloride solution, dried over magnesium sulfate, filtered and evaporated. After triturating in heptane, 208 mg (83%) of 3-{3-butoxy-4-[3-(4-ethanesulfonyloxy-3-methoxyphenyl)propyl]phenyl)propanoic acid are obtained in the form of white crystals with a melting point of 64° C.

NMR ($^1$H, CDCl$_3$): 0.98 (t, J=7.4 Hz, 3H); 1.46 (m, 2H); 1.53 (t, J=7.4 Hz, 3H); 1.77 (m, 2H); 1.90 (m, 2H); 2.60-2.69 (m, 6H); 2.92 (t, J=7.6 Hz, 2H); 3.29 (q, J=7.4 Hz, 2H); 3.85 (s, 3H); 3.93 (t, J=6.3 Hz, 2H); 6.66-6.71 (m, 2H); 6.76-6.78 (m, 2H); 7.02 (d, J=7.5 Hz, 1H); 7.19 (d, J=8.7 Hz, 1H).

Example 7

3-[4-{3-[4-(butane-1-sulfonyloxy)-3-methoxyphenyl]propyl}-3-(3-fluorobenzyloxy)phenyl]propanoic acid a—3-benzyloxy-4-iodobenzaldehyde 47 ml (411 mmol) of benzyl chloride are added to a solution of 93 g (374 mmol) of 3-hydroxy-4-iodobenzaldehyde in 600 ml of methyl ethyl ketone in the presence of 103 g (748 mmol) of potassium carbonate. The reaction medium is heated at 78° C. for 18 hours. The solid is filtered off and the solvent is evaporated off. The solid obtained is washed with heptane and 114 g (90%) of 3-benzyloxy-4-iodobenzaldehyde are obtained in the form of white crystals.

b—methyl(E)-3-(3-benzyloxy-4-iodophenyl)acrylate 170 g (506 mmol) of methyl (triphenylphosphoranylidene) acetate are added to a solution of 114 g (337 mmol) of 3-benzyloxy-4-iodobenzaldehyde in 570 ml of toluene. The reaction mixture is refluxed for 2 hours. The solvent is evaporated off and the oil obtained is purified by chromatography on a column of silica eluted with a 50/50 heptane/dichloromethane mixture. 115 g (87%) of methyl(E)-3-(3-benzyloxy-4-iodophenyl)acrylate are obtained in the form of pale yellow crystals.

c—butyl (4-allyl-2-methoxyphenyl)methanesulfonate 5.2 ml (40 mmol) of butanesulfonyl chloride are added to a solution of 6 g (36 mmol) of eugenol and 5.5 ml (43 mmol) of triethylamine in 100 ml of dichloromethane, cooled beforehand to −20° C. After stirring at room temperature for 3 hours, the reaction medium is treated with water and ethyl acetate. The organic phase is dried over magnesium sulfate, filtered and evaporated. 10.8 g (100%) of butyl (4-allyl-2-methoxyphenyl)methanesulfonate are obtained.

d—methyl(E)-3-(3-benzyloxy-4-{(E)-3-[4-(butane-1-sulfonyloxy)-3-methoxyphenyl]propenyl}-phenyl) acrylate 0.3 g (0.8 mmol) of 2-(dicyclohexylphosphino)biphenyl, 0.1 g (0.4 mmol) of palladium (II) acetate and then 3.4 ml (25 mmol) of triethylamine are added to a solution of 7 g (3 mmol) of butyl (4-allyl-2-methoxyphenyl)methanesulfonate and 8.1 g (20 mmol) of methyl(E)-3-(3-benzyloxy-4-iodophenyl)acrylate in 80 ml of dimethylformamide. The reaction mixture is heated at 90° C. for 15 hours. After adding 20 ml of water and then extracting with ethyl acetate, the organic phases are combined, washed with saturated sodium chloride solution, dried over sodium sulfate, filtered and evaporated. 11 g (100%) of ethyl 4-{(E)-3-[4-(butane-1-sulfonyloxy)-3-methoxyphenyl]propenyl}-3-butoxybenzoate are obtained.

e—methyl 3-(4-{3-[4-(butane-1-sulfonyloxy)-3-methoxyphenyl]propyl}-3-hydroxyphenyl)propanoate 11 g (20 mmol) of methyl(E)-3-(3-benzyloxy-4-{(E)-3-[4-(butane-1-sulfonyloxy)-3-methoxyphenyl] propenyl}phenyl)acrylate are dissolved in 100 ml of methanol and 1.1 g (10% massique) palladium-on-charcoal are then added. The reaction medium est placed under 1 atmosphere of hydrogen for 24 hours, and then filtered through Celite and rinsed with dichloromethane, and the filtration liquors are concentrated. The residue is purified by chromatography on a column of silica eluted with an 8/2 heptane/ethyl acetate mixture. 8 g (73%) of methyl 3-(4-{3-[4-(butane-1-sulfonyloxy)-3-methoxyphenyl]propyl}-3-hydroxyphenyl)propanoate are obtained.

f—methyl 3-[4-{3-[4-(butane-1-sulfonyloxy)-3-methoxyphenyl]propyl}-3-(3-fluorobenzyloxy)phenyl]propanoate 0.2 g (1.2 mmol) of potassium carbonate and then 0.1 ml (0.9 mmol) of 3-fluorobenzyl bromide are added to a solution of 0.4 g (0.8 mmol) of methyl 3-(4-{3-[4-(butane-1-sulfonyloxy)-3-methoxyphenyl]propyl}-3-hydroxyphenyl)propanoate. The reaction medium is stirred at 80° C. for 15 hours and then treated with water and extracted with ethyl acetate. The organic phase is dried over magnesium sulfate, filtered and concentrated.

The residue obtained is purified by chromatography on a column of silica eluted with an 8/2 heptane/ethyl acetate mixture. 0.27 g (60%) of methyl 3-[4-{3-[4-(butane-1-sulfonyloxy)-3-methoxyphenyl]propyl}-3-(3-fluorobenzyloxy)phenyl]propanoate is obtained.

g—3-[4-{3-[4-(butane-1-sulfonyloxy)-3-methoxyphenyl]propyl}-3-(3-fluorobenzyloxy)phenyl]propanoic acid 0.4 g (1 mmol) of lithium hydroxide monohydrate is added to a solution of 0.3 g (0.5 mmol) of corresponding methyl 3-[4-{3-[4-(butane-1-sulfonyloxy)-3-methoxyphenyl]propyl}-3-(3-fluorobenzyloxy)phenyl]propanoate in 10 ml of a tetrahydrofuran/methanol/water mixture (5/1/1). The reaction medium is stirred at room temperature for 15 hours, treated with water, acidified to pH 4 with acetic acid and extracted with ethyl acetate. The organic phase is dried over magnesium sulfate, filtered and concentrated. The residue obtained is purified by chromatography on a column of silica eluted with a 97/3 dichloromethane/methanol mixture. 0.23 g (77%) of 3-[4-{3-[4-(butane-1-sulfonyloxy)-3-methoxyphenyl]propyl}-3-(3-fluorobenzyloxy)phenyl]propanoic acid is obtained in the form of a colorless oil.

NMR ($^1$H, CDCl$_3$): 0.89 (t, J=7.3 Hz, 3H); 1.40 (m, 2H); 1.83-1.93 (m, 4H); 2.55-2.63 (m, 6H); 2.84 (t, J=7.6 Hz, 2H); 3.18 (m, 2H); 3.74 (s, 3H); 4.97 (s, 2H); 6.66-6.69 (m, 4H); 6.93 (m, 1H); 7.00 (d, J=7.5 Hz, 1H); 7.06-7.17 (m, 3H); 7.26 (m, 1H).

Example 8

3-[4-{3-[4-(butane-1-sulfonyloxy)-3-methoxyphenyl]propyl}-3-(4-fluorobenzyloxy)phenyl]propanoic acid a—methyl 3-[4-{3-[4-(butane-1-sulfonyloxy)-3-methoxyphenyl]propyl}-3-(4-fluorobenzyloxy)phenyl]propanoate 0.2 g (1.2 mmol) of potassium carbonate and then 0.1 ml (0.9 mmol) of 4-fluorobenzyl bromide are added to a solution of 0.4 g (0.8 mmol) of methyl 3-(4-{3-[4-(butane-1-sulfonyloxy)-3-methoxyphenyl]propyl}-3-hydroxyphenyl)propanoate (prepared according to Example 7e). The reaction medium is stirred at 80° C. for 15 hours and then treated with water and extracted with ethyl acetate. The organic phase is dried over magnesium sulfate, filtered and concentrated.

The residue obtained is purified by chromatography on a column of silica eluted with an 8/2 heptane/ethyl acetate mixture. 0.3 g (65%) of methyl 3-[4-{3-[4-(butane-1-sulfonyloxy)-3-methoxyphenyl]propyl}-3-(4-fluorobenzyloxy)phenyl]propanoate are obtained.

b—3-[4-{3-[4-(butane-1-sulfonyloxy)-3-methoxyphenyl]propyl}-3-(4-fluorobenzyloxy)phenyl]propanoic acid 0.4 g (1 mmol) of lithium hydroxide monohydrate is added to a solution of 0.3 g (0.5 mmol) of corresponding methyl 3-[4-{3-[4-(butane-1-sulfonyloxy)-3-methoxyphenyl]propyl}-3-(4-fluorobenzyloxy)phenyl]propanoate in 10 ml of a tetrahydrofuran/methanol/water mixture (5/1/1). The reaction medium is stirred at room temperature for 15 hours, treated with water, acidified to pH 4 with acetic acid and extracted with ethyl acetate. The organic phase is dried over magnesium sulfate, filtered and concentrated. The residue obtained is purified by chromatography on a column of silica eluted with a 97/3 dichloromethane/methanol mixture. 0.24 g (85%) of 3-[4-{3-[4-(butane-1-sulfonyloxy)-3-methoxyphenyl]propyl}-3-(4-fluorobenzyloxy)phenyl]propanoic acid is obtained in the form of a colorless oil.

NMR ($^1$H, CDCl$_3$): 0.89 (t, J=7.4 Hz, 3H); 1.43 (m, 2H); 1.81-1.92 (m, 4H); 2.53-2.61 (m, 6H); 2.84 (t, J=7.6 Hz, 1H); 3.19 (m, 2H); 3.73 (s, 3H); 4.93 (s, 2H); 6.64-6.69 (m, 4H); 6.97-7.01 (m, 3H); 7.08 (d, J=8 Hz, 1H); 7.18-7.31 (m, 2H).

Example 9

3-(4-{3-[4-(butane-1-sulfonyloxy)-3-methoxyphenyl]propyl}-3-cyclopropylmethoxyphenyl)propanoic acid a—methyl 3-(4-{3-[4-(butane-1-sulfonyloxy)-3-methoxyphenyl]propyl}-3-cyclopropylmethoxyphenyl)propanoate 0.2 g (1.2 mmol) of potassium carbonate and then 0.12 g (0.9 mmol) of bromomethyl-cyclopropane are added to a solution of 0.4 g (0.8 mmol) of methyl 3-(4-{3-[4-(butane-1-sulfonyloxy)-3-methoxyphenyl]propyl}-3-hydroxyphenyl)propanoate (prepared according to Example 7e). The reaction medium is stirred at 80° C. for 15 hours and then treated with water and extracted with ethyl acetate. The organic phase is dried over magnesium sulfate, filtered and concentrated.

The residue obtained is purified by chromatography on a column of silica eluted with an 8/2 heptane/ethyl acetate mixture. 0.26 g (61%) of methyl 3-(4-{3-[4-(butane-1-sulfonyloxy)-3-methoxyphenyl]propyl}-3-cyclopropylmethoxyphenyl)propanoate is obtained.

b—3-(4-{3-[4-(butane-1-sulfonyloxy)-3-methoxyphenyl]propyl}-3-cyclopropylmethoxyphenyl)propanoic acid 0.4 g (1 mmol) of lithium hydroxide monohydrate is added to a solution of 0.26 g (0.5 mmol) of corresponding methyl 3-(4-{3-[4-(butane-1-sulfonyloxy)-3-methoxyphenyl]propyl}-3-cyclopropylmethoxyphenyl)propanoate in 10 ml of a tetrahydrofuran/methanol/water mixture (5/1/1). The reaction medium is stirred at room temperature for 15 hours, treated with water, acidified to pH 4 with acetic acid and extracted with ethyl acetate. The organic phase is dried over magnesium sulfate, filtered and concentrated. The residue obtained is purified by chromatography on a column of silica eluted with a 97/3 dichloromethane/methanol mixture. 0.24 g (100%) of 3-(4-{3-[4-(butane-1-sulfonyloxy)-3-methoxyphenyl]propyl}-3-cyclopropylmethoxyphenyl)propanoic acid is obtained in the form of a colorless oil.

NMR ($^1$H, CDCl$_3$): 0.25 (m, 2H); 0.52 (m, 2H); 0.90 (t, J=7.3 Hz, 3H); 1.17 (m, 1H); 1.42 (m, 2H); 2.56-2.61 (m, 6H); 2.83 (t, J=7.5 Hz, 2H); 3.72 (d, J=6.6 Hz, 2H); 3.78 (s, 3H); 6.58 (s, 1H); 6.63 (dd, J=1.4 Hz, J=7.6 Hz, 1H); 6.71-6.73 (m, 2H); 6.96 (d, J=7.6 Hz, 1H); 7.11 (d, J=8.6 Hz, 1H).

Example 10

3-[4-{3-[4-(butane-1-sulfonyloxy)-3-methoxyphenyl]propyl}-2-(3-methoxybenzyloxy)phenyl]propanoic acid a—3-hydroxy-4-iodobenzoic acid 1319 g (1.52 mol) of commercial 9.6% sodium hypochlorite solution are added dropwise to a solution of 200 g (1.45 mol) of 3-hydroxybenzoic acid, 61 g (1.52 mol) of sodium hydroxide powder and 228 g (1.52 mol) of sodium iodide in 2 l of methanol cooled beforehand to 0° C. The reaction medium is stirred at room temperature for 72 hours. After evaporating off the methanol, the solution is cooled to 10° C. and acidified with aqueous hydrochloric acid solution to pH 2. The mixture is stirred for 2 hours and the product precipitates. The product is filtered off, washed thoroughly with water and dried under vacuum at 50° C. 150 g (39%) of 3-hydroxy-4-iodobenzoic acid are obtained in the form of a white solid.

b—methyl 3-hydroxy-4-iodobenzoate

A solution of 140 g (530 mmol) of 3-hydroxy-4-iodobenzoic acid and 20.2 g (110 mmol) of para-toluenesulfonic acid in 900 ml of methanol is refluxed for 18 hours. After cooling, 700 ml of water are added and the medium is stirred for 18 hours. The product precipitates and is filtered off. After drying under vacuum at 50° C., 137 g (93%) of methyl 3-hydroxy-4-iodobenzoate are obtained in the form of a white solid.

c—methyl 3-benzyl-4-iodobenzoate 47 ml (411 mmol) of benzyl chloride are added to a solution of 104 g (374 mmol) of methyl 3-hydroxy-4-iodobenzoate and 103 g (748 mmol) of potassium carbonate in 600 ml of methyl ethyl ketone, and the reaction medium is then refluxed for 8 hours. After cooling, the reaction medium is filtered, the precipitate is rinsed with ethyl acetate and the filtrate is evaporated to dryness. The residue is taken up in a mixture of water and ethyl acetate. The organic phase is dried over sodium sulfate, filtered and evaporated. 139 g (100%) of methyl 3-benzyl-4-iodobenzoate are obtained in the form of a white solid.

d—3-benzyloxy-4-iodobenzyl alcohol

A solution of 139 g (374 mmol) of methyl 3-benzyl-4-iodobenzoate in 550 ml of tetrahydrofuran is added dropwise to a solution of 12.9 g (563 mmol) of lithium borohydride in 150 ml of tetrahydrofuran and the reaction medium is then refluxed for 3 hours. After cooling, 300 ml of saturated aqueous ammonium chloride solution are added and the reaction medium is extracted with ethyl acetate. The organic phase is washed with water, dried over sodium sulfate, filtered and evaporated. 125 g (97%) of 3-benzyloxy-4-iodobenzyl alcohol are obtained in the form of white crystals.

e—3-benzyloxy-4-iodobenzaldehyde

A solution of 125 g (370 mmol) of 3-benzyloxy-4-iodobenzyl alcohol and 160 g (1.84 mol) of manganese dioxide in 750 ml of dichloromethane is stirred at room temperature for 18 hours. Since the reaction is not complete, a further 160 g (1.84 mol) of manganese dioxide are added and the medium is stirred for 6 hours. The reaction medium is filtered through Celite and the filtrate is then concentrated under vacuum. 114 g (92%) of 3-benzyloxy-4-iodobenzaldehyde are obtained in the form of a yellow oil.

f—methyl(E)-3-(2-benzyloxy-4-iodophenyl)acrylate 170 g (506 mmol) of methyl triphenylphosphoranylideneacetate are added portionwise to a solution of 114 g (337 mmol) of 3-benzyloxy-4-iodobenzaldehyde in 570 ml of toluene and the reaction medium is refluxed for two hours. After cooling, the reaction medium is filtered through Celite and then concentrated under vacuum. The residue obtained is purified by chromatography on a column of silica eluted with an 80/20 heptane/ethyl acetate mixture. 113 g (85%) of methyl(E)-3-(2-benzyloxy-4-iodophenyl)acrylate are obtained in the form of a yellow powder.

g—4-allyl-2-methoxyphenyl 1-butanesulfonate 13 ml (0.1 mol) of butanesulfonyl chloride are added dropwise to a solution of 15 g (0.09 mol) of eugenol and 16 ml (0.11 mol) of triethylamine in 150 ml of dichloromethane cooled beforehand to −20° C. The reaction mixture is stirred for 4 hours at room temperature. The reaction is treated by adding 50 ml of water and extracting with dichloromethane. The organic phase is dried over sodium sulfate, filtered and evaporated. The residue is purified by chromatography on a column of silica eluted with a 90/10 heptane/ethyl acetate mixture. 24.3 g (74%) of 4-allyl-2-methoxyphenyl 1-butane-1-sulfonate are obtained in the form of a yellow oil.

h—methyl(E)-3-(2-benzyloxy-4-{(E)-3-[4-(butane-1-sulfonyloxy)-3-methoxyphenyl]propenyl}-phenyl)acrylate 71 mg (0.2 mmol) of 2-(dicyclohexylphosphino)biphenyl and 23 mg (0.1 mmol) of palladium acetate are added to a solution of 2 g (5.07 mmol) of methyl(E)-3-(2-benzyloxy-4-iodophenyl)acrylate, 1.1 ml (7.6 mmol) of triethylamine and 2.9 g (5.07 mmol) of 4-allyl-2-methoxyphenyl 1-butane-1-sulfonate in 20 ml of dimethylformamide. The reaction mixture is heated at 80° C. for 4 hours. The reaction is treated by addition of 50 ml of water and then extracted with ethyl acetate. The organic phases are combined, washed with saturated sodium chloride solution, dried over sodium sulfate and filtered, and the solvents are then evaporated off. The residue is purified by chromatography on a column of silica eluted with a 90/10 heptane/ethyl acetate mixture. 2.53 g (91%) of methyl(E)-3-(2-benzyloxy-4-{(E)-3-[4-(butane-1-sulfonyloxy)-3-methoxyphenyl]propenyl}phenyl)acrylate are obtained in the form of a yellow oil.

i—methyl 3-(4-{3-[4-(butane-1-sulfonyloxy)-3-methoxyphenyl]propyl}-2-hydroxyphenyl)propanoate 78 mg (10% mass equivalent) of 10% palladium-on-charcoal are added to a solution of 780 mg (1.4 mmol) of methyl (E)-3-(2-benzyloxy-4-{(E)-3-[4-(butane-1-sulfonyloxy)-3-methoxyphenyl]propenyl}phenyl)acrylate in 8 ml of methanol. The reaction mixture is placed under an atmospheric pressure of hydrogen at room temperature for 16 hours and then filtered through Celite and rinsed with dichloromethane. The solvents are evaporated off and the residue is then purified by chromatography on a column of silica eluted with a 60/40 heptane/ethyl acetate mixture. 610 mg (94%) of methyl 3-(4-{3-[4-(butane-1-sulfonyloxy)-3-methoxyphenyl]propyl}-2-hydroxyphenyl)propanoate are obtained in the form of a colorless oil.

j—methyl 3-[4-{3-[4-(butane-1-sulfonyloxy)-3-methoxyphenyl]propyl}-2-(3-methoxybenzyloxy)phenyl]propanoate 68 μl (0.5 mmol) of 3-methoxybenzyl chloride are added to a solution of 200 mg (0.5 mmol) of methyl 3-(4-{3-[4-(butane-1-sulfonyloxy)-3-methoxyphenyl]propyl}-2-hydroxyphenyl)propanoate and 89 mg (0.5 mmol) of potassium carbonate in 5 ml of methyl ethyl ketone, and the reaction medium is then heated at 70° C. for 48 hours. After cooling, water is added and the reaction medium is then extracted with ethyl acetate. The organic phase is dried over sodium sulfate, filtered and evaporated. The residue obtained is purified by chromatography on a column of silica eluted with a 7/3 heptane/ethyl acetate mixture. 120 mg (48%) of methyl 3-[4-{3-[4-(butane-1-sulfonyloxy)-3-methoxyphenyl]propyl}-2-(3-methoxybenzyloxy)phenyl]propanoate are obtained.

k—3-[4-{3-[4-(butane-1-sulfonyloxy)-3-methoxyphenyl]propyl}-2-(3-methoxybenzyloxy)phenyl]propanoic acid 0.62 ml (0.62 mmol) of 1M lithium hydroxide solution is added to a solution of 181.6 mg (0.31 mmol) of methyl 3-[4-{3-[4-(butane-1-sulfonyloxy)-3-methoxyphenyl]propyl}-2-(3-methoxybenzyloxy)phenyl]propanoate in 5 ml of tetrahydrofuran. The reaction mixture is stirred overnight at room temperature. The reaction is treated by adding 10 ml of water, acidified with hydrochloric acid and then extracted with ethyl acetate. The organic phases are combined and dried over sodium sulfate. After evaporating off the solvents, the residue is purified by chromatography on a column of silica eluted with a 95/5 dichloromethane/methanol mixture. 162 mg (92%) of 3-[4-{3-[4-(butane-1-sulfonyloxy)-3-methoxyphenyl]propyl}-2-(3-methoxybenzyloxy)phenyl]propanoic acid are obtained in the form of a yellow oil.

NMR $^1$H (δ, CDCl$_3$): 0.90 (t, J=7.3 Hz, 3H); 1.42 (m, 2H); 1.85-1.93 (m, 4H); 2.52 (m, 4H); 2.91 (t, J=7.3 Hz, 2H); 3.2 (m, 2H); 3.73 (s, 3H); 3.78 (s, 3H); 4.99 (s, 2H); 6.65-6.69 (m, 3H); 6.77 (m, 1H); 6.93 (m, 1H); 7.12 (d, J=8 Hz, 1H); 7.19 (m, 1H); 7.22-7.24 (m, 2H).

Example 11

3-(4-{3-[4-(butane-1-sulfonyloxy)-3-methoxyphenyl]propyl}-2-butoxyphenyl)propanoic acid a—methyl 3-(4-{3-[4-(butane-1-sulfonyloxy)-3-methoxyphenyl]propyl}-2-butoxyphenyl)propanoate ml (0.95 mmol) of iodobutane is added to a solution of 400 mg (0.86 mmol) of methyl 3-(4-{3-[4-(butane-1-sulfonyloxy)-3-methoxyphenyl]propyl}-2-hydroxyphenyl)propanoate (prepared according to Example 10i) and 178 mg (1.29 mmol) of potassium carbonate in 10 ml of methyl ethyl ketone, and the reaction mixture is then heated at 70° C. for 18 hours. The reaction is treated by adding 20 ml of water and then extracted with ethyl acetate. The organic phases are combined, dried over sodium sulfate, filtered and evaporated. The residue is purified by chromatography on a column of silica eluted with a 70/30 heptane/ethyl acetate mixture. 179 mg (40%) of methyl 3-(4-{3-[4-(butane-1-sulfonyloxy)-3-methoxyphenyl]propyl}-2-butoxyphenyl)propanoate are obtained in the form of a colorless oil.

3-(4-{3-[4-(butane-1-sulfonyloxy)-3-methoxyphenyl]propyl}-2-butoxyphenyl)propanoic acid 0.66 ml (0.66 mmol) of aqueous 1M lithium hydroxide solution is added to a solution of 171 mg (0.33 mmol) of methyl 3-(4-{3-[4-(butane-1-sulfonyloxy)-3-methoxyphenyl]propyl}-2-butoxyphenyl)propanoate in 3 ml of tetrahydrofuran, and the reaction mixture is then stirred for 18 hours at room temperature. After evaporating to dryness, the reaction medium is taken up in 10 ml of water and acidified with acetic acid to pH 4, and then extracted with ethyl acetate. The organic phases are combined, dried over sodium sulfate and filtered. The solvents are evaporated off and the residue is then purified by chromatography on a column of silica eluted with a 99/1 dichloromethane/methanol mixture. 99 mg (60%) of 3-(4-{3-[4-(butane-1-sulfonyloxy)-3-methoxyphenyl]propyl}-2-butoxyphenyl)propanoic acid are obtained in the form of a yellow oil.

NMR $^1$H (δ, CDCl$_3$): 0.97 (t, J=7.3 Hz, 3H); 1.01 (t, J=7.3 Hz, 3H); 1.49-1.55 (m, 4H); 1.80 (m, 2H); 1.82-1.90 (m, 4H); 2.62-2.68 (m, 6H); 2.94 (t, J=7.5 Hz, 2H); 3.30 (t, J=7.8 Hz, 2H); 3.87 (s, 3H); 3.98 (t, J=6.3 Hz, 2H); 6.67 (s, 1H); 6.70 (d, J=7.6 Hz, 1H); 6.78-6.80 (m, 2H); 7.08 (d, J=7.5 Hz, 1H); 7.21 (d, J=8.7 Hz, 1H).

Example 12

Cross-Curve PPAR Transactivation Tests

The activation of PPAR receptors with an agonist (activator) in HeLN cells leads to the expression of a reporter gene, luciferase, which, in the presence of a substrate, generates light. The modulation of the PPAR receptors is measured by quantifying the luminescence produced after incubating the cells in the presence of a reference agonist. The ligands displace the agonist from its site. The measurement of the activity is performed by quantifying the light produced. This measurement makes it possible to determine the modulatory activity of the compounds according to the invention by determining the constant that is the affinity of the molecule for the PPAR receptor. Since this value can fluctuate depending on the basal activity and the expression of the receptor, it is referred to as Kd apparent (KdApp in nM).

To determine this constant, "cross curves" of the test product against a reference agonist are produced in a 96-well plate: 10 concentrations of the test product plus a concentration 0 are arranged in a line, and 7 concentrations of the agonist plus a concentration 0 are arranged in a column. This is 88 measurement points for 1 product and 1 receptor. The remaining 8 wells are used for repeatability controls.

In each well, the cells are in contact with a concentration of the test product and a concentration of the reference agonist, 2-(4-{2-[3-(2,4-difluorophenyl)-1-heptylureido]ethyl}phenylsulfanyl)-2-methylpropionic acid for PPARα, {2-methyl-4-[4-methyl-2-(4-trifluoromethylphenyl)thiazol-5-ylmethylsulfanyl]phenoxy}acetic acid for PPARδ and 5-{-4-[2-(methylpyrid-2-ylamino)ethoxy]benzyl}thiazolidine-2,4-dione for PPARγ. Measurements are also taken for total agonist controls with the same products.

The HeLN cell lines used are stable transfectants containing the plasmids ERE-βGlob-Luc-SV-Neo (reporter gene) and PPAR (α, δ, γ) Gal-hPPAR. These cells are inoculated into 96-well plates at a rate of 10 000 cells per well in 100 µl of DMEM medium without phenol red and supplemented with 10% of defatted calf serum. The plates are then incubated at 37° C. and 7% $CO_2$ for 16 hours.

The various dilutions of the test products and of the reference ligand are added at a rate of 5 µl per well. The plates are then incubated for 18 hours at 37° C. and 7% $CO_2$. The culture medium is removed by turning over and 100 µl of a 1:1 PBS/luciferin mixture are added to each well. After 5 minutes, the plates are read by the luminescence detector.

These cross curves make it possible to determine the AC50 values (concentration at which 50% activation is observed) of the reference ligand at various concentrations of test product. These AC50 values are used to calculate the Schild regression by plotting a straight line corresponding to the Schild equation ("quantitation in receptor pharmacology" Terry P. Kenakin, *Receptors and Channels*, 2001, 7, 371-385), which allows the Kd app values (in nM) to be obtained.

Transactivation Results:

| Compounds | PPAR alpha Kd app (nM) | PPARs delta Kd app (in nM) | PPAR gamma Kd app (in nM) |
|---|---|---|---|
| Reference 1: 2-(4-{2-[3-(2,4-difluorophenyl)-1-heptylureido]-ethyl}phenyl-sulfanyl)-2-methyl-propionic acid | 200 | n.a. | n.a. |
| Reference 2: {2-methyl-4-[4-methyl-2-(4-trifluoromethyl-phenyl)thiazol-5-ylmethyl-sulfanyl]phenoxy}acetic acid | n.a. | 10 | n.a. |
| Reference 3: 5-{4-[2-(methylpyridin-2-ylamino)ethoxy]benzyl}-thiazolidine-2,4-dione | n.a. | n.a. | 30 |
| Example 5 | 9999 | 9999 | 8 |

These results show the affinity of the compounds for the PPAR receptors and more particularly the specificity of the affinity of the compounds of the invention for the PPARγ subtype, compared with the affinity of the compounds for the PPARα subtype or for the PPARδ subtype.

Example 13

Compositions

Various specific formulations based on the compounds according to the invention are illustrated in this example.

Oral Route:

(a) 0.2 g Tablet:

| | |
|---|---|
| Compound of Example 5 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable Suspension in 5 ml Ampules:

| | |
|---|---|
| Compound of Example 4 | 0.001 g |
| Glycerol | 0.500 g |
| 70% sorbitol | 0.500 g |
| Sodium saccharinate | 0.010 g |
| Methyl parahydroxybenzoate | 0.040 g |
| Flavoring | qs |
| Purified water | qs 5 ml |

(c) 0.2 g Tablet:

| | |
|---|---|
| Compound of Example 1 | 0.050 g |
| Lactose monohydrate | 0.132 g |
| Crosspovidone | 0.007 g |
| Povidone | 0.005 g |
| Aerosil 200 | 0.004 g |
| Magnesium stearate | 0.002 g |

(d) Drinkable Suspension in 10 ml Ampules:

| | |
|---|---|
| Compound of Example 4 | 0.200 g |
| Glycerol | 1.000 g |
| 70% sorbitol | 1.000 g |
| Sodium saccharinate | 0.010 g |
| Methyl parahydroxybenzoate | 0.080 g |
| Flavoring | qs |
| Purified water | qs 10 ml |

B—Topical Route:

(a) Ointment:

| | |
|---|---|
| Compound of Example 5 | 0.020 g |
| Isopropyl myristate | 81.700 g |
| Fluid petroleum jelly oil | 9.100 g |
| Silica ("Aerosil 200") | 9.180 g |

(b) Ointment:

| Compound of Example 3 | 0.300 g |
|---|---|
| White petroleum jelly codex | qs 100 g |

(c) Nonionic Water-in-Oil Cream:

| Compound of Example 7 | 0.100 g |
|---|---|
| Mixture of emulsifying lanolin alcohols, waxes and oils ("Anhydrous Eucerin") | 39.900 g |
| Methyl parahydroxybenzoate | 0.075 g |
| Propyl parahydroxybenzoate | 0.075 g |
| Sterile demineralized water | qs 100 g |

(d) Lotion:

| Compound of Example 8 | 0.100 g |
|---|---|
| Polyethylene glycol (PEG 400) | 69.900 g |
| 95% ethanol | 30.000 g |

(e) Hydrophobic Ointment:

| Compound of Example 5 | 0.300 g |
|---|---|
| Isopropyl myristate | 36.400 g |
| Silicone oil ("Rhodorsil 47 V 300") | 36.400 g |
| Beeswax | 13.600 g |
| Silicone oil ("Abil 300.000 cSt") | qs 100 g |

(f) Nonionic Oil-in-Water Cream:

| Compound of Example 5 | 1.000 g |
|---|---|
| Cetyl alcohol | 4.000 g |
| Glyceryl monostearate | 2.500 g |
| PEG 50 stearate | 2.500 g |
| Shea butter | 9.200 g |
| Propylene glycol | 2.000 g |
| Methyl parahydroxybenzoate | 0.075 g |
| Propyl parahydroxybenzoate | 0.075 g |
| Sterile demineralized water | qs 100 g |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A 3-phenylpropanoic compound having the general formula (I) below:

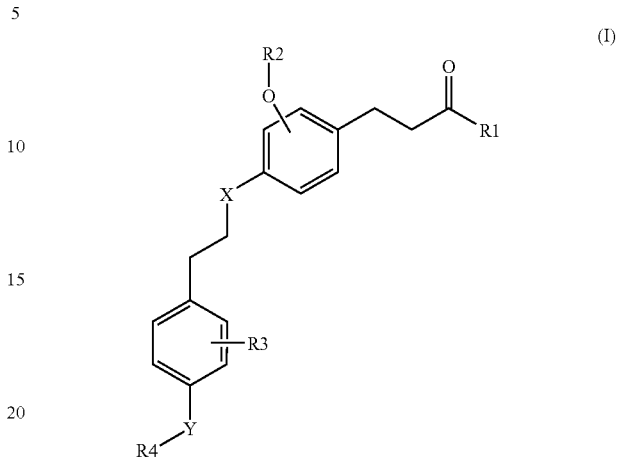

in which:
- $R_1$ is a hydroxyl radical or an alkoxy radical;
- $R_2$ is a hydrogen atom, an alkyl radical, a cycloalkyl radical, an optionally substituted aralkyl radical or a polyether radical;
- $R_3$ is a hydrogen atom, a halogen, an alkyl radical or an alkoxy radical;
- $R_4$ is an alkyl radical, an optionally substituted aryl radical or an optionally substituted aralkyl radical;
- X is an oxygen atom or a radical $CH_2$;
- Y is an oxygen atom, a radical $NR_5$ or a radical $OSO_2$, $OCO$, $NR_5CO$ or $NR_5SO_2$;
- $R_5$ is a hydrogen atom or an alkyl radical;

and also the salts thereof with a pharmaceutically acceptable acid or base, and the pharmaceutically acceptable solvates and hydrates thereof.

2. A compound as defined by claim 1, in the form of an alkali metal or alkaline-earth metal salt or of a salt with an organic amine.

3. A compound as defined by claim 1, wherein, when it bears an amine function, it is in the form of a mineral acid salt or an organic acid salt.

4. A compound as defined by claim 1, comprising an alkyl radical that is a linear or branched saturated hydrocarbon-based chain containing from 1 to 12 carbon atoms.

5. A compound as defined by claim 1, comprising an alkyl radical selected from among methyl, ethyl, propyl, isopropyl, butyl, isobutyl, tert-butyl, pentyl, isoamyl, amyl and hexyl radicals.

6. A compound as defined by claim 1, comprising an cycloalkyl radical that is a saturated cyclic hydrocarbon-based chain containing from 3 to 7 carbon atoms.

7. A compound as defined by claim 1, comprising an optionally substituted aryl radical selected from among phenyl and naphthyl optionally substituted with one or more atoms or groups of atoms selected from among an alkyl, an alkoxy, a halogen, a hydroxyl, a cyano, a trifluoromethyl and a nitro substituent.

8. A compound as defined by claim 1, comprising an optionally substituted aralkyl radical selected from among benzyl and phenethyl optionally substituted with one or more atoms or groups of atoms selected from an alkyl, an alkoxy, a halogen, a hydroxyl, a cyano, a trifluoromethyl and a nitro substituent.

9. A compound as defined by claim 1, comprising a halogen atom selected from among fluorine, chlorine, bromine and iodine atoms.

10. A compound as defined by claim 1, comprising an alkoxy radical selected from among methoxy, ethoxy, isopropyloxy, n-propyloxy, tert-butoxy, n-butoxy, n-pentyloxy and n-hexyloxy radicals.

11. A compound as defined by claim 1, comprising an polyether radical selected from among radicals containing from 1 to 7 carbon atoms interrupted with at least one oxygen atom.

12. A compound as defined by claim 1, selected from the group consisting of:
 1. 3-{4-[3-(4-benzyloxy-3-methoxyphenyl)propyl]-3-butoxyphenyl}propanoic acid;
 2. 3-{3-butoxy-4-[3-(4-ethoxy-3-methoxyphenyl)propyl]phenyl}propanoic acid;
 3. 3-{3-butoxy-4-[3-(4-butoxy-3-methoxyphenyl)propyl]phenyl}propanoic acid;
 4. 3-{3-butoxy-4-[3-(4-methanesulfonyloxy-3-methoxyphenyl)propyl]phenyl}propanoic acid;
 5. 3-(4-{3-[4-(butane-1-sulfonyloxy)-3-methoxyphenyl]propyl}-3-butoxyphenyl)propanoic acid;
 6. 3-{3-butoxy-4-[3-(4-ethanesulfonyloxy-3-methoxyphenyl)propyl]phenyl}propanoic acid;
 7. 3-[4-{3-[4-(butane-1-sulfonyloxy)-3-methoxyphenyl]propyl}-3-(3-fluorobenzyloxy)phenyl]propanoic acid;
 8. 3-[4-{3-[4-(butane-1-sulfonyloxy)-3-methoxyphenyl]propyl}-3-(4-fluorobenzyloxy)phenyl]propanoic acid;
 9. 3-(4-{3-[4-(butane-1-sulfonyloxy)-3-methoxyphenyl]propyl}-3-cyclopropylmethoxyphenyl)propanoic acid;
 10. 3-[4-{3-[4-(butane-1-sulfonyloxy)-3-methoxyphenyl]propyl}-2-(3-methoxybenzyloxy)phenyl]propanoic acid;
 11. 3-(4-{3-[4-(butane-1-sulfonyloxy)-3-methoxyphenyl]propyl}-2-butoxyphenyl)propanoic acid;
 12. methyl 3-[4-[3-(4-acetylaminophenyl)propyl]-3-(2-methoxyethoxy)phenyl]propanoate;
 13. methyl 3-(4-{3-[4-(acetylmethylamino)phenyl]propyl}-3-methoxyphenyl)propanoate;
 14. 3-(4-{3-[4-(butane-1-sulfonyloxy)phenyl]propyl}-3-hydroxyphenyl)propanoic acid;
 15. 3-(4-{3-[4-(butane-1-sulfonylamino)phenyl]propyl}-3-butoxyphenyl)propanoic acid;
 16. 3-[4-(2-{4-[(3-chlorobenzoyl)methylamino]phenyl}ethoxy)-3-(2-ethoxyethoxy)phenyl]propanoic acid;
 17. 3-[3-butoxy-4-(2-{4-[methyl-(2-p-tolylethanesulfonyl)amino]phenyl}ethoxy)phenyl]propanoic acid;
 18. 3-(4-{3-[4-(butane-1-sulfonyloxy)-3-methoxyphenyl]propyl}-3-butoxyphenyl)propanoic acid;
 19. methyl 3-{3-butoxy-4-[3-(4-ethoxy-3-fluorophenyl)propyl]phenyl}propanoate;
 20. 3-[4-{3-[4-(butane-1-sulfonyloxy)-2-methoxyphenyl]propyl}-3-(2-ethoxyethoxy)phenyl]propanoic acid;
 21. 3-(4-{3-[3-chloro-4-(hexane-1-sulfonyloxy)phenyl]propyl}-3-ethoxyphenyl)propanoic acid;
 22. 3-{4-[2-(3-chloro-4-ethoxyphenyl)ethoxy]-3-methoxyphenyl}propanoic acid; and
 23. 4-{3-[4-(2-carboxyethyl)-2-methoxyphenyl]propyl}phenyl butyrate.

13. A compound as defined by claim 1, having at least one of the following characteristics:
 $R_1$ is a hydroxyl radical,
 $R_2$ is an alkyl radical or a radical polyether,
 $R_3$ is a hydrogen atom, an alkoxy radical or a halogen,
 $R_4$ is an alkyl radical,
 X is an oxygen atom or a group $CH_2$,
 Y is a sequence —$NR_5SO_2$ or a sequence —$OSO_2$, $R_5$ being a hydrogen atom or an alkyl radical.

14. A compound as defined by claim 1, having at least one of the following characteristics:
 $R_1$ is a hydroxyl radical,
 $R_2$ is a lower alkyl radical,
 $R_3$ is a lower alkoxy radical,
 $R_4$ is a lower alkyl radical,
 X is an oxygen atom or a group $CH_2$,
 Y is a sequence —$OSO_2$.

15. A cosmetic composition comprising at least one of the compounds as defined by claim 1, formulated into a cosmetically applicable, physiologically acceptable support therefor.

16. The cosmetic composition as defined by claim 15, having a concentration of compound(s) ranging from 0.001% to 3% by weight relative to the total weight of the composition.

17. A regime or regimen for body or hair hygiene, comprising topically applying thereon a thus effective amount of the cosmetic composition as defined by claim 15.

18. A regime or regimen for regulating and/or restoring skin lipid metabolism, comprising administering to an individual in need of such treatment, a thus effective amount of a compound as defined by claim 1.

19. A pharmaceutical composition comprising at least one compound as defined by claim 1, formulated into a physiologically acceptable medium therefor.

20. The pharmaceutical composition as defined by claim 19, having a concentration of compound(s) ranging from 0.001% to 10% by weight relative to the total weight of the composition.

21. The pharmaceutical composition as defined by claim 20, having a concentration of compound(s) ranging from 0.01% to 1% by weight relative to the total weight of the composition.

22. A regime or regimen for activating the receptors of PPAR type of an individual in need of such treatment, comprising administering thereto a thus effective amount of at least one 3-phenylpropanoic compound as defined by claim 1.

* * * * *